(12) United States Patent
Ogomi et al.

(10) Patent No.: US 9,244,135 B2
(45) Date of Patent: Jan. 26, 2016

(54) MAGNETIC SENSOR DEVICE

(75) Inventors: Tomokazu Ogomi, Tokyo (JP); Hiroyuki Asano, Tokyo (JP); Toshiaki Shoji, Tokyo (JP); Takeshi Musha, Tokyo (JP); Jin Inoue, Tokyo (JP); Masaaki Okada, Tokyo (JP); Miki Kagano, Tokyo (JP); Kazuya Makabe, Tokyo (JP); Kenji Shimohata, Tokyo (JP); Takeshi Kishimoto, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 168 days.

(21) Appl. No.: 14/009,441

(22) PCT Filed: May 11, 2012

(86) PCT No.: PCT/JP2012/062126
§ 371 (c)(1),
(2), (4) Date: Oct. 2, 2013

(87) PCT Pub. No.: WO2012/157558
PCT Pub. Date: Nov. 22, 2012

(65) Prior Publication Data
US 2014/0028308 A1 Jan. 30, 2014

(30) Foreign Application Priority Data

May 16, 2011 (JP) .................................. 2011-109628
Mar. 29, 2012 (JP) .................................. 2012-077356

(51) Int. Cl.
*G01R 33/09* (2006.01)
*G01D 5/14* (2006.01)
(Continued)

(52) U.S. Cl.
CPC ................ *G01R 33/09* (2013.01); *G01D 5/147* (2013.01); *G01R 33/096* (2013.01); *G07D 7/04* (2013.01); *G01N 27/72* (2013.01)

(58) Field of Classification Search
CPC ...... G01R 33/02; G01R 33/09; G01R 33/096; G01R 33/098; G01R 33/093; G07D 7/00; G07D 7/004; G07D 7/02; G07D 7/04; G07D 7/06; H01L 43/02; H01L 43/08
USPC .......................................... 324/252
See application file for complete search history.

(56) References Cited

U.S. PATENT DOCUMENTS 5,638,222 A * 6/1997 Shigehara ..................... 359/814
5,703,733 A 12/1997 Suzuki et al.
(Continued)

FOREIGN PATENT DOCUMENTS

CN 101666863 A 3/2010
CN 101666864 A 3/2010
(Continued)

OTHER PUBLICATIONS

Office Action issued Feb. 6, 2015 in Russian Patent Application No. 2013151002/28(079501) (with English translation).
(Continued)

*Primary Examiner* — Melissa Koval
*Assistant Examiner* — Rahul Maini
(74) *Attorney, Agent, or Firm* — Oblon, McClelland, Maier & Neustadt, L.L.P.

(57) ABSTRACT

A magnetic sensor device includes a first magnet and a second magnet that are disposed on mutually opposing sides of a conveyance path, and one of poles of the first magnet faces an opposite pole of the second magnet. The first magnet and the second magnet generate a cross magnetic field whose strength in a spacing direction, which is orthogonal to a conveying direction, is within a predetermined range. An AMR element is located in a magnetic field in which the strength of the cross magnetic field in the spacing direction is within a predetermined range, and detects, as change in a resistance value, change in the cross magnetic field caused by an object to be detected. A multilayer board outputs the change in the resistance value detected by the AMR element to a processing circuit.

3 Claims, 22 Drawing Sheets

(51) Int. Cl.
*G07D 7/04* (2006.01)
*G01N 27/72* (2006.01)

(56) References Cited

U.S. PATENT DOCUMENTS

| | | | |
|---|---|---|---|
| 6,310,475 B1* | 10/2001 | Kawase et al. | 324/235 |
| 6,900,713 B2* | 5/2005 | Kasashima et al. | 335/207 |
| 7,019,607 B2* | 3/2006 | Busch | H03K 17/97 335/205 |
| 2003/0030522 A1 | 2/2003 | Kasashima et al. | |
| 2007/0186666 A1* | 8/2007 | Ruehrig et al. | 73/779 |
| 2010/0156405 A1 | 6/2010 | Furukawa et al. | |
| 2013/0119980 A1* | 5/2013 | Ogomi | G01R 33/091 324/252 |
| 2013/0127457 A1* | 5/2013 | Musha | B82Y 25/00 324/252 |

FOREIGN PATENT DOCUMENTS

| | | |
|---|---|---|
| DE | 10 2008 058 538 A1 | 5/2010 |
| EP | 0 662 667 A2 | 7/1994 |
| EP | 1 292 029 A2 | 3/2003 |
| EP | 2 180 329 A2 | 4/2010 |
| EP | 2 320 196 A1 | 5/2011 |
| JP | 57 175054 | 11/1982 |
| JP | 58 2994 | 1/1983 |
| JP | 62 41266 | 10/1987 |
| JP | 1-250084 A | 10/1989 |
| JP | 5 332703 | 12/1993 |
| JP | 6 167302 | 6/1994 |
| JP | 6 231336 | 8/1994 |
| JP | 6-350159 A | 12/1994 |
| JP | 7 12908 | 1/1995 |
| JP | 8 86848 | 4/1996 |
| JP | 8 178937 | 7/1996 |
| JP | 8 249602 | 9/1996 |
| JP | 9 152303 | 6/1997 |
| JP | 10 19601 | 1/1998 |
| JP | 10 153454 | 6/1998 |
| JP | 2001 21631 | 1/2001 |
| JP | 2002 131406 | 5/2002 |
| JP | 2003 60256 | 2/2003 |
| JP | 2005 129009 | 5/2005 |
| JP | 2008 145379 | 6/2008 |
| KR | 10-2010-0027980 A | 3/2010 |
| RU | 2 175 455 C2 | 10/2001 |
| SU | 920596 A1 | 4/1982 |
| WO | 2008 146809 | 12/2008 |
| WO | 2010 052797 | 5/2010 |
| WO | 2012 014546 | 2/2012 |
| WO | 2012 015012 | 2/2012 |

OTHER PUBLICATIONS

Korean Office Action issued Sep. 24, 2014 in Patent Application No. 10-2013-7029138 with English Translation.

International Search Report Issued Aug. 14, 2012 in PCT/JP12/62126 Filed May 11, 2012.

Extended European Search Report issued Mar. 12, 2015 in Patent Application No. 12784930.5.

Combined Chinese Office Action and Search Report issued Jun. 11, 2015 in Patent Application No. 201280023413.0 (with partial English language translation and English translation of categories of cited documents).

Shen Dong-ping, et al., "Application of Anisotropic Magnetoresistive Sensor for Vehicle Detection" Journal of Xiamen University (Natural Science), vol. 48, No. 6, Nov. 2009, pp. 827-829.

Office Action issued on Sep. 1, 2015 in the corresponding Japanese Patent Application No. 2012-077356 (with English Translation).

Office Action mailed Nov. 4, 2015, in Korean Patent Application 10-2015-7022947 (with English Translation).

\* cited by examiner

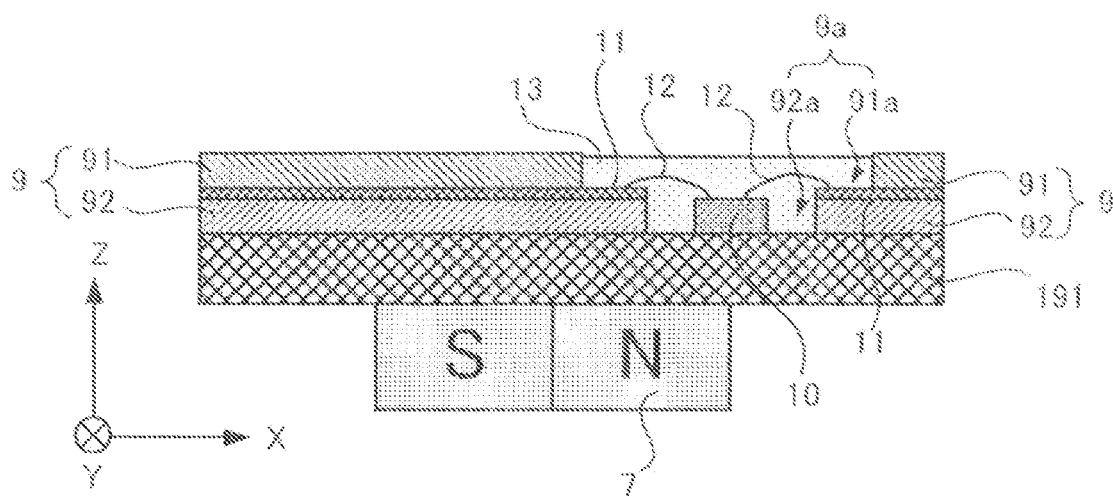
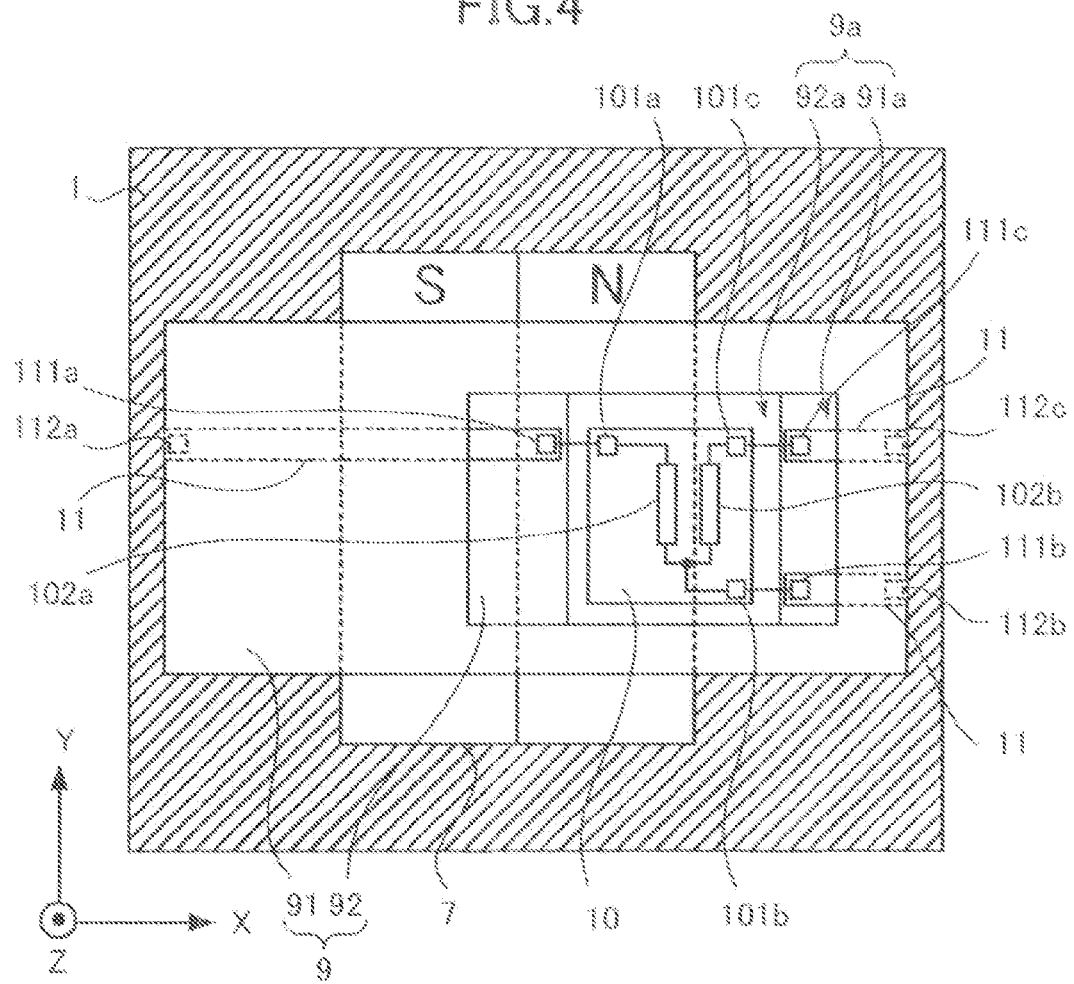

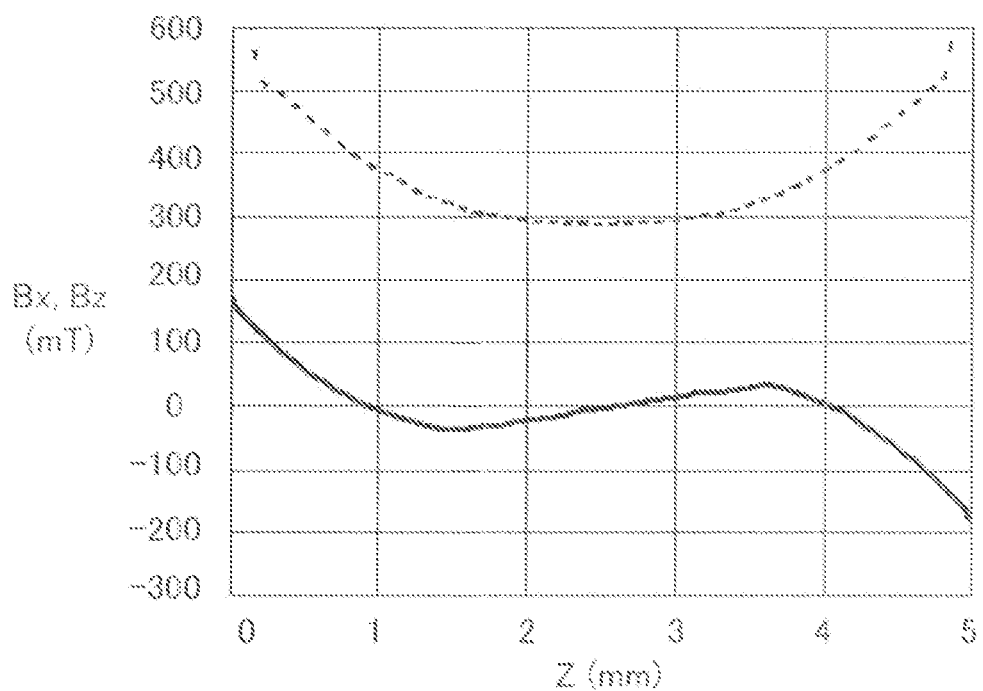
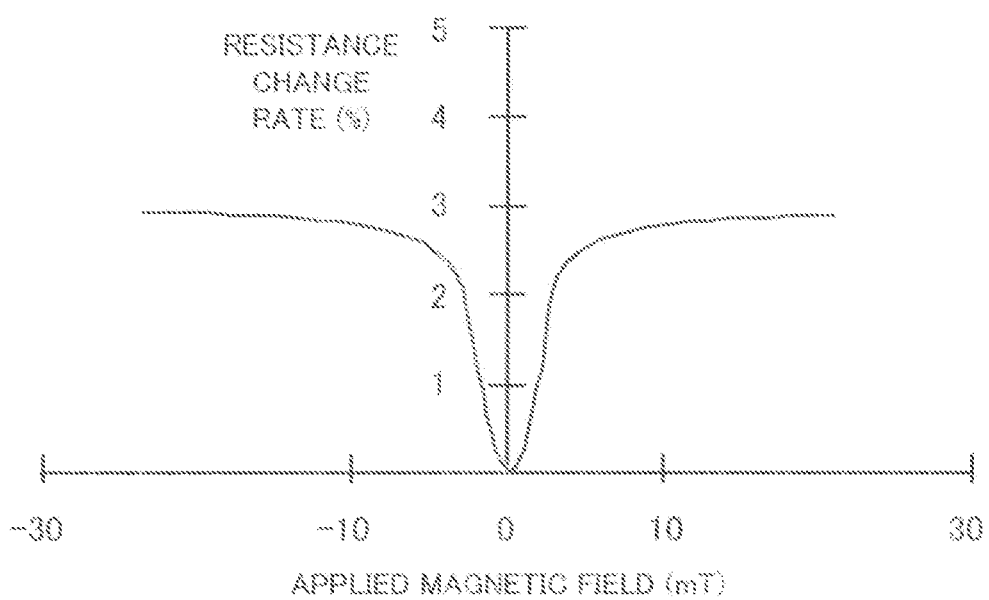

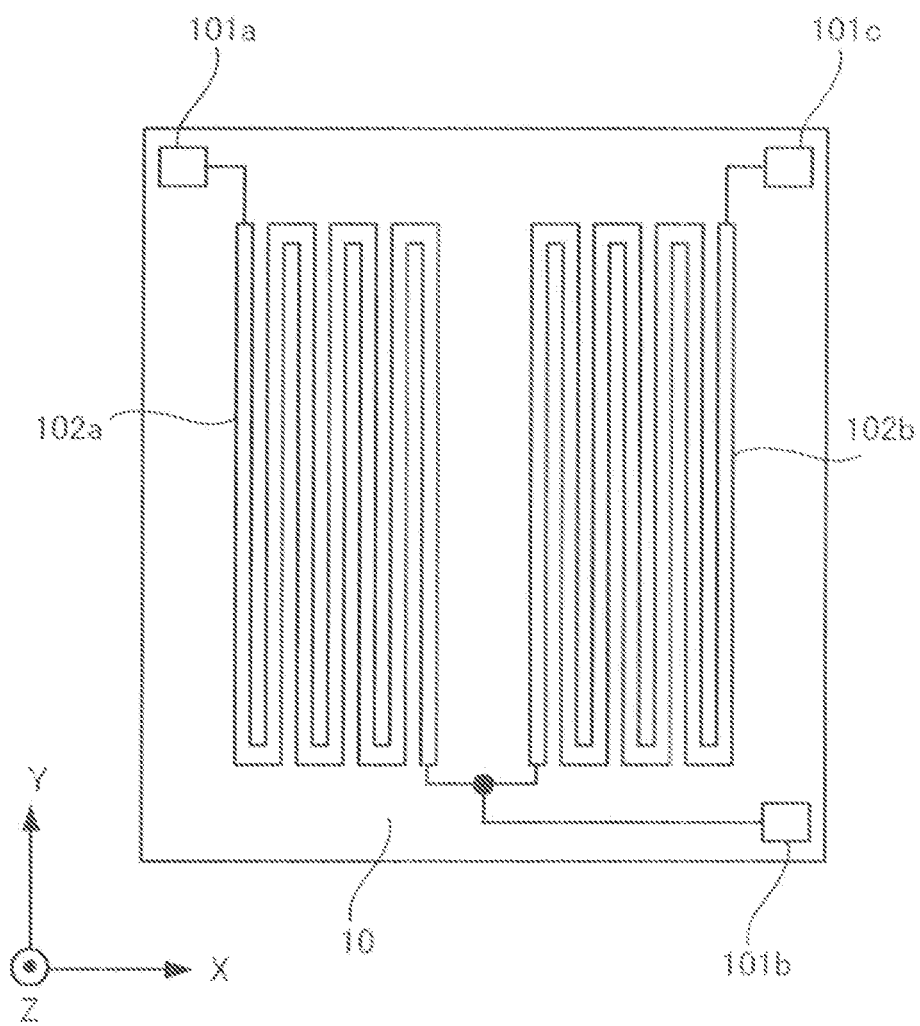

MAGNETIC SENSOR DEVICE

TECHNICAL FIELD

The present invention relates to a magnetic sensor device that detects the magnetic pattern of an object to be detected.

BACKGROUND ART

A magnetic sensor device is a sensor device that uses a magnetoresistance effect element having a characteristic whereby its resistance value changes corresponding to a magnetic field strength. The magnetization amount of the magnetic pattern of a paper medium such as paper money is subtle. In order to improve sensitivity to detect the magnetic pattern of an object to be detected whose magnetization amount is subtle, the magnetic sensor device needs to be configured in such a way that the magnetic sensor device uses an anisotropic magnetoresistance effect element, which has a higher detection sensitivity than a semiconductor magnetoresistance effect element, and the anisotropic magnetoresistance effect element is disposed under a magnetic field strength in which sensitivity is the highest, and the object to be detected passes through a ferromagnetic field.

However, in a magnetic sensor device using an anisotropic magnetoresistance effect element, the anisotropic magnetoresistance effect element is saturated at a magnetic field strength of about 10 mT. Therefore, there is a problem in that it is difficult to dispose the anisotropic magnetoresistance effect element in a magnetic field strength environment in which the anisotropic magnetoresistance effect element is not saturated and the detection sensitivity is the highest.

In addition, in a non-contact magnetic sensor device, the object to be detected such as a paper sheet medium and a magnetoresistance effect element are apart from each other by a predetermined distance, making smaller an output of change in the resistance value of the magnetoresistance effect element which, in turn, causes deterioration of detection sensitivity.

In order to solve such a problem, Patent Literature 1 discloses a magnetic sensor in which the position of a permanent magnet is adjusted so that the bias magnetic field strength in the magnetic sensing direction of the ferromagnetic thin-film magnetoresistance element applied by a detecting magnetic field by the permanent magnet has a magnetic flux amount of a saturated magnetic field or lower.

CITATION LIST

Patent Literature

Patent Literature 1: Unexamined Japanese Patent Application Kokai Publication No. 2008-145379

SUMMARY OF INVENTION

Technical Problem

However, Patent Literature 1 does not disclose the specific arrangement of the permanent magnet so that the bias magnetic field strength in the magnetic sensing direction of the ferromagnetic thin-film magnetoresistance element has a magnetic flux amount of a saturated magnetic field or lower. In addition, in order to improve the detection sensitivity of a non-contact magnetic sensor device, the magnetic force of the bias magnet must be increased to apply a suitable bias magnetic field on an anisotropic magnetoresistance effect element, and also the magnetic field strength of a conveyance path in which the object to be detected is conveyed must be increased. However, there is a problem in that if change in the magnetic field strength caused by an object to be detected is small, for example, like the case in which the object to be detected passes through apart from the bias magnet than an anisotropic magnetoresistance effect element, the output signal from the anisotropic magnetoresistance effect element is small.

This invention was made in order to solve the above problem, and has an objective to improve sensitivity to detect the magnetic pattern of an object to be detected when the object to be detected having the magnetic pattern and a magnetoresistance effect element are not in contact with each other, that is, apart from each other by a predetermined distance.

Solution to Problem

The magnetic sensor device according to the present invention includes a conveyance path for conveying an object to be detected having a magnetic pattern, a magnet having poles each facing the conveyance path, first magnetic bodies each in contact with each of side surfaces orthogonal to the conveying direction of the object to be detected, of side surfaces of the magnet, and at least one second magnetic body located on a side opposite to the first magnetic bodies with respect to the conveyance path. The magnetic sensor device further includes: a magnetoresistance effect element located between the second magnetic body and the conveyance path in a cross magnetic field that has magnetic field strength within a predetermined range in a spacing direction and that is generated by the first magnetic bodies and the second magnetic body, the magnetoresistance effect element to detect, as change in the resistance value, changes in a component in the conveying direction in the cross magnetic field, the change being caused by the magnetic pattern of the object to be detected, the spacing direction being a direction orthogonal to the conveying direction in the conveyance path and being a direction that vertically passes through the magnetic pattern; and an outputter connected to the magnetoresistance effect element and to output the change in the resistance value detected by the magnetoresistance effect element.

Advantageous Effects of Invention

The present invention improves sensitivity to detect the magnetic pattern of an object to be detected when the object to be detected having the magnetic pattern and the magnetoresistance effect element are not in contact with each other, that is, apart from each other by a predetermined distance.

BRIEF DESCRIPTION OF DRAWINGS

FIG. 3 is an enlarged view illustrating a state in which a multilayer board and an AMR element are mounted on a metal carrier in the magnetic sensor device according to the First Embodiment;

FIG. 4 is a top view of the multilayer board and the AMR element of the magnetic sensor device according to the First Embodiment, seen from the conveyance path side;

FIG. 9 is a graph illustrating change in a magnetic field strength in the conveying direction and change in a magnetic field strength in the spacing direction over a distance in the spacing direction in the conveyance path of the magnetic sensor device according to the First Embodiment;

FIG. 10 is a graph illustrating relationship between a magnetic field applied on the AMR element and a resistance change rate;

FIG. 11 is a top view of an AMR element having meander-shaped resistors in the magnetic sensor device according to the First Embodiment;

DESCRIPTION OF EMBODIMENTS

First Embodiment

Figure 1:
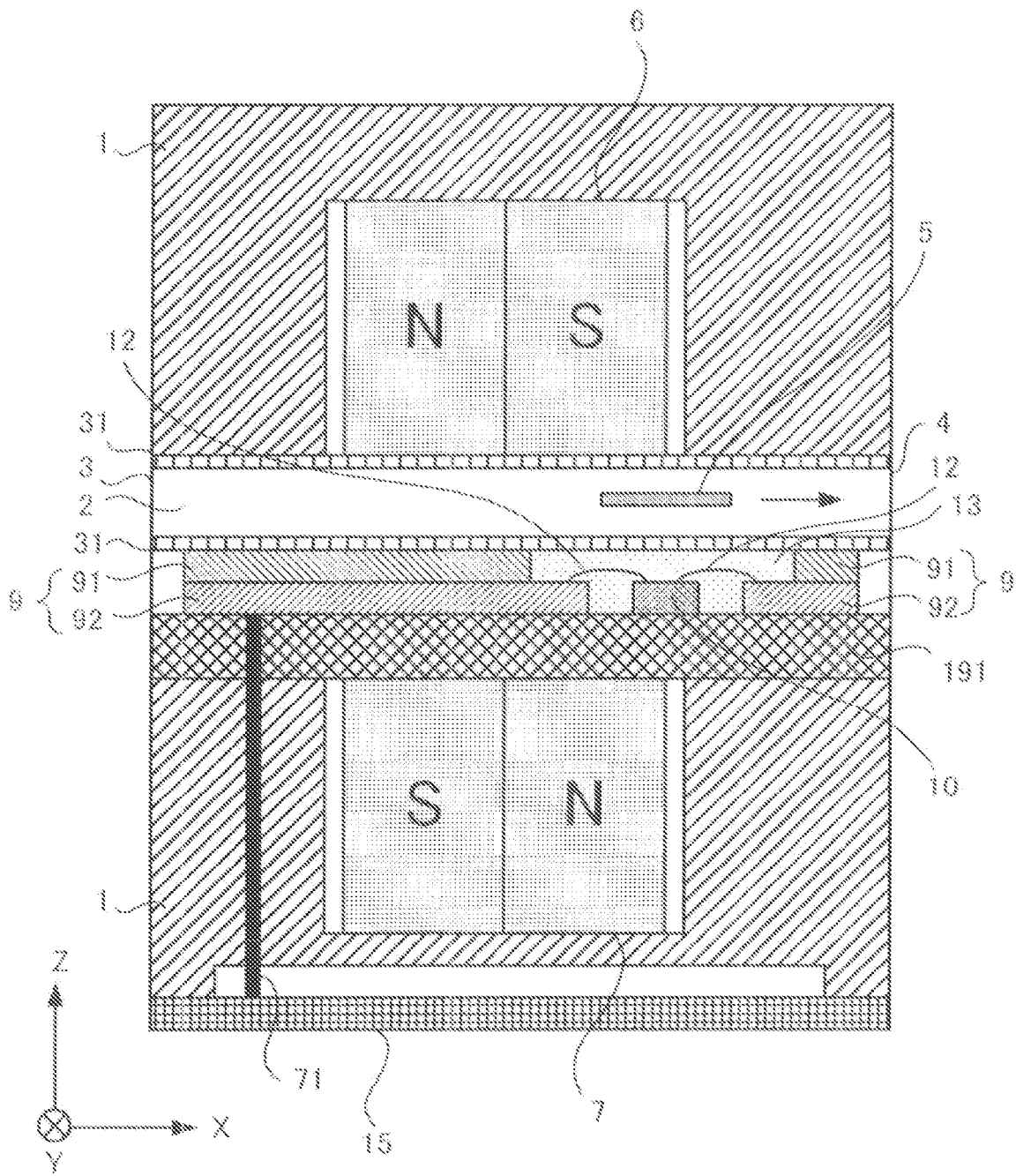
FIG. 1 is a cross-sectional view along a conveying direction of a magnetic sensor device according to First Embodiment of the present invention.
Figure 2:
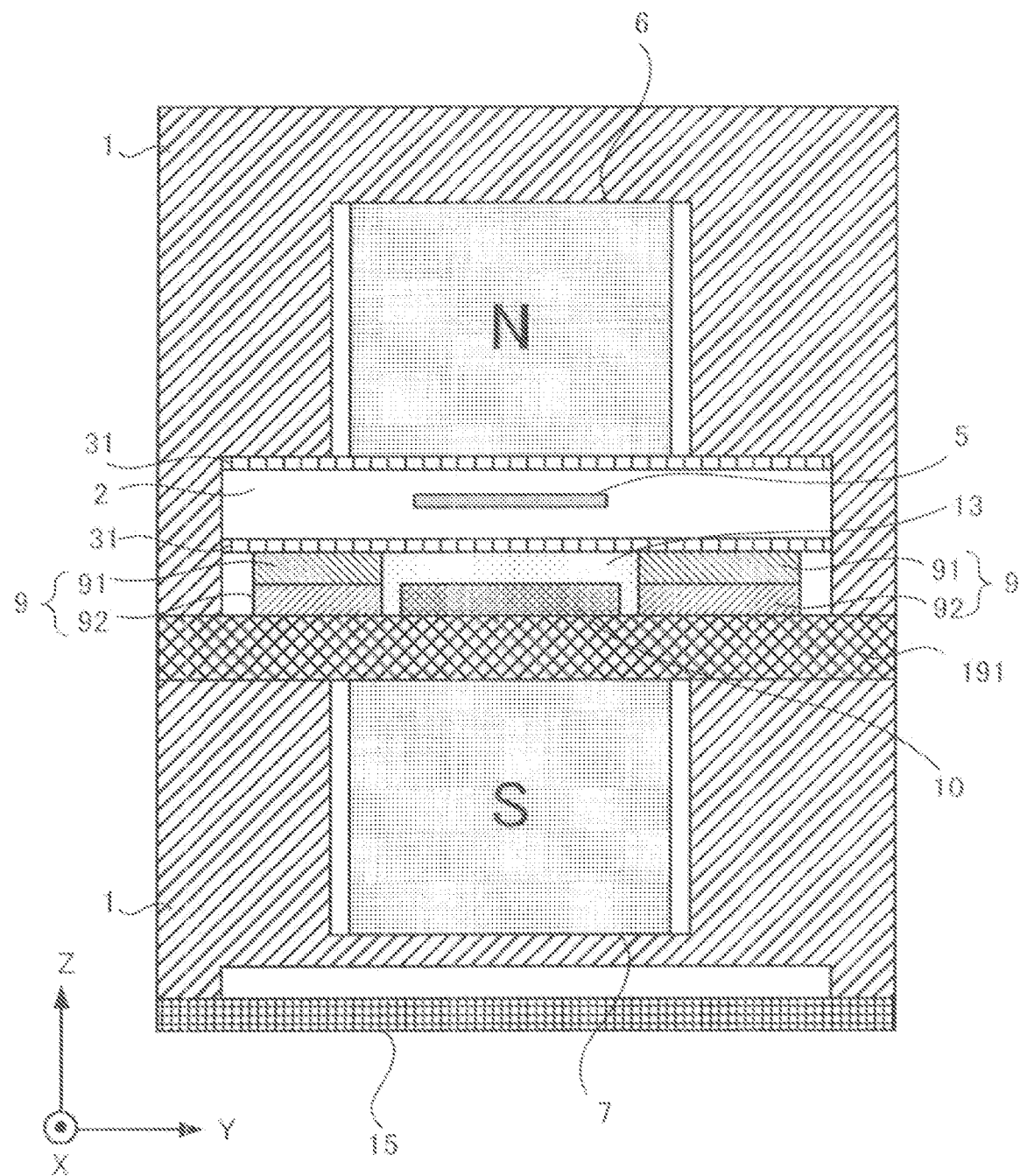
FIG. 2 is s cross-sectional view along a direction orthogonal to the conveying direction of the magnetic sensor device according to the First Embodiment.

FIG. 1 is a cross-sectional view along a conveying direction of a magnetic sensor device according to First Embodiment of the present invention. FIG. 2 is a cross-sectional view along a direction orthogonal to the conveying direction of the magnetic sensor device according to the First Embodiment. In drawings, an X axis direction is the conveying direction, a Y axis direction is the reading width direction, and a Z axis direction is the spacing direction. The conveying direction, the reading width direction and the spacing direction are orthogonal to one another. The spacing direction is a direction that vertically passes through the magnetic pattern of an object to be detected 5. A conveyance path 2 is for conveying the object to be detected 5 that is a paper sheet medium such as paper money. The object to be detected 5 is inserted through a first slit 3 formed across the reading width direction on one side (sidewall) of a housing 1. The object to be detected 5 is conveyed in the conveying direction indicated by an arrow in FIGS. 1 and 2 on the conveyance path 2 by a conveyor that is not illustrated, and discharged through a second slit 4 formed across the reading width direction on the other side (sidewall).

A first magnet 6 and a second magnet 7, which are permanent magnets, are located on mutually opposing sides of the conveyance path 2, one pole of the first magnet 6 facing an opposite pole of the second magnet 7. That is, the north pole of the first magnet 6 faces the south pole of the second magnet 7, and the south pole of the first magnet 6 faces the north pole of the second magnet 7. The first magnet 6 and the second magnet 7 are disposed apart from the object to be detected 5. Electric shields 31 are provided in such a way that each of the electric shields 31 is in contact with the first magnet 6 side or the second magnet 7 side of the conveyance path 2.

A metal carrier 191, which is a non-magnetic body, is provided in contact with the conveyance path 2 side of the second magnet 7. On the surface of the metal carrier 191 and apart from the object to be detected 5 are provided a multilayer board 9 made of resin such as glass epoxy and an AMR (anisotropic magnetoresistance effect) element 10. The AMR element 10 includes a resistor on the surface thereof, and has a characteristic wherein its resistance value changes according to change in the magnetic field orthogonal to the direction of an electric current that flows through the resistor.

Figure 5:
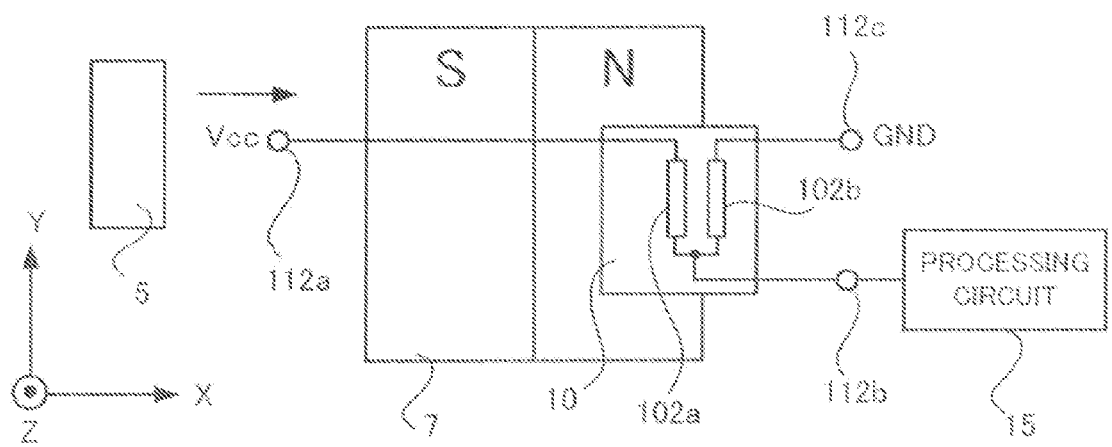
FIG. 5 is a diagram illustrating connection of the AMR element and an external circuit in the magnetic sensor device according to the First Embodiment.

FIG. 3 is an enlarged view illustrating a state in which the multilayer board and the AMR element are mounted on the metal carrier in the magnetic sensor device according to the First Embodiment. FIG. 3 is a partially enlarged view of FIG. 1. FIG. 4 is a top view of the multilayer board and the AMR element of the magnetic sensor device according to the First Embodiment, seen from the conveyance path side. FIG. 5 is a diagram illustrating connection of the AMR element and an external circuit in the magnetic sensor device according to the First Embodiment. The multilayer board 9 includes at least a first layer board 91 and a second layer board 92, and is secured to the metal carrier 191. The multilayer board 9 has a hole 9a. The hole 9a is composed of a hole 91a of the first layer board and a hole 92a of the second layer board. The opening of the hole 91a of the first layer board is larger than the opening of the hole 92a of the second layer board. Alternatively, the multilayer board 9 may include a third or more layer boards.

The AMR element 10 is bonded with adhesive to the surface of the metal carrier 191 that is exposed to the hole 92a of the second layer board, and is surrounded by the multilayer board 9. The hole 91a of the first layer board and the hole 92a of the second layer board are sealed with a resin 13 in such a way that the resin does not overflow from the surface of the first layer board 91. Electrodes 101a to 101c of the AMR element 10 are connected to electrodes 111a to 111c provided on the surface of the second layer board 92 that is exposed to the hole 91a of the first layer board, respectively, by metal wires 12 that are electric connection means. The electrodes 111a to 111c are connected via a transmission line 11 to connection pads 112a to 112c provided on the back surface of the multilayer board 9.

Each of the resistor 102a and resistor 102b of the AMR element 10 is formed in such a way that the long side of its rectangular shape extends along the reading width direction. The resistors 102a, 102b are made of, for example, thin films. The resistor 102a and the resistor 102b are connected in series to each other; the connection point of the resistor 102a and the resistor 102b is connected to the electrode 101b; the electrode 101b is connected via the metal wire 12 to the electrode 111b, which is connected via the connection pad 112b and a cable 71 to a processing circuit 15 that processes signals. The other end of the resistor 102a is connected to the electrode 101a; the electrode 101a is connected via the metal wire 12 to the electrode 111a, which is connected via the connection pad 112a to a DC (Direct Current) power supply voltage Vcc. The other end of the resistor 102b is connected to the electrode 101c; the electrode 101c is connected via the metal wire 12 to the electrode 111c, which is DC grounded via the connection pad 112c.

Figure 6:
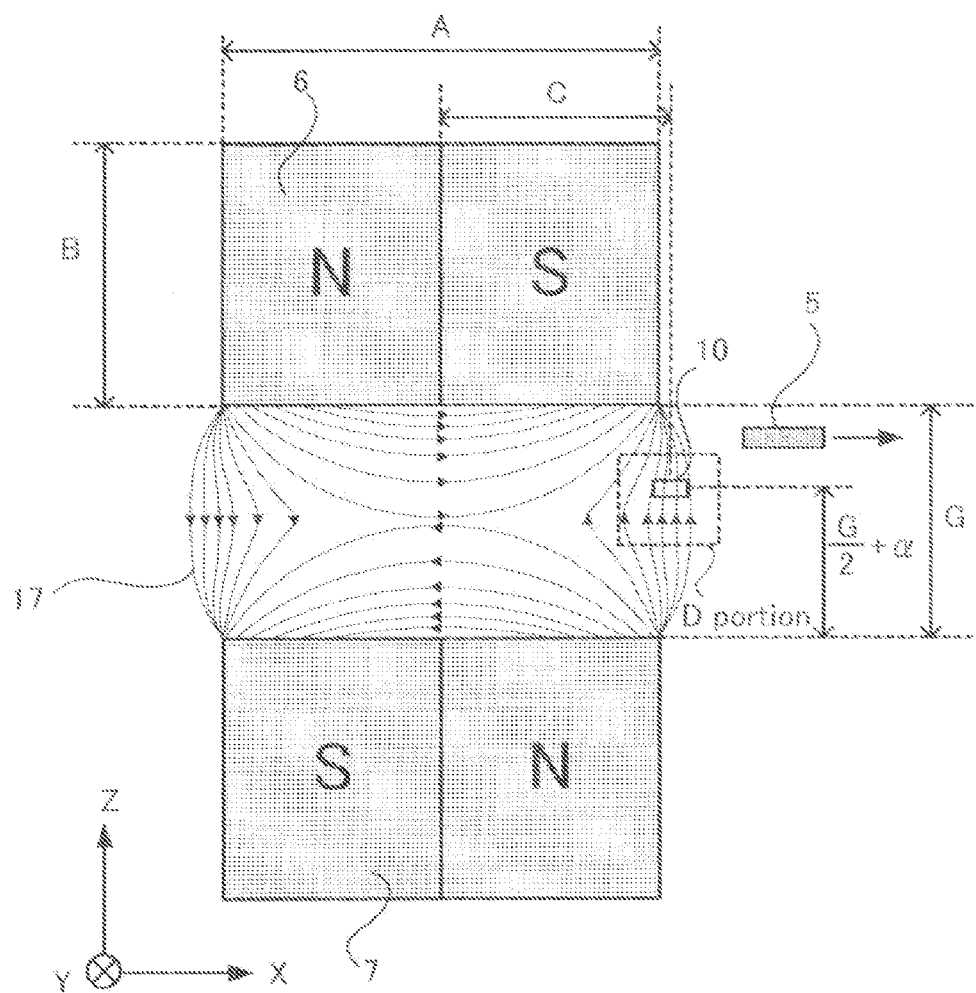
FIG. 6 is a diagram illustrating a magnetic field distribution generated by a first magnet and a second magnet in the conveyance path in the magnetic sensor device according to the First Embodiment.
Figure 7:
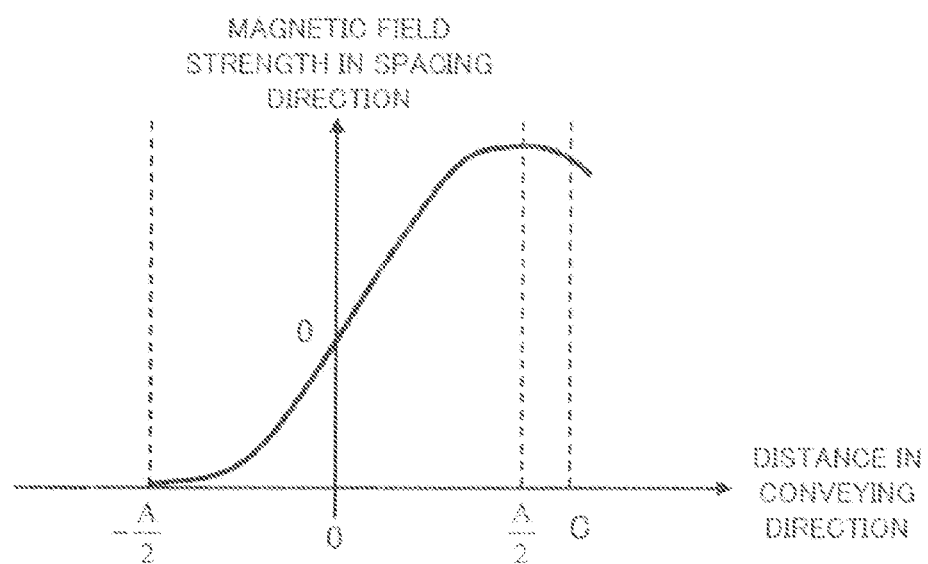
FIG. 7 is a graph illustrating change in a magnetic field strength in a spacing direction over a distance in the conveying direction in the conveyance path of the magnetic sensor device according to the First Embodiment.

FIG. 6 is a diagram illustrating a magnetic field distribution generated by the first magnet and the second magnet in the conveyance path of the magnetic sensor device according to the First Embodiment. FIG. 7 is a graph illustrating change in the magnetic field strength in the spacing direction over a distance in the conveying direction in the conveyance path of the magnetic sensor device according to the First Embodiment. In FIG. 7, the horizontal axis indicates a distance in the conveying direction with the center in the conveying direction of the first magnet 6 being 0, and the vertical axis indicates a magnetic field strength in the spacing direction. FIG. 8 is a diagram of a vector of a magnetic field line for describing a detection principle of the magnetic sensor device according to the First Embodiment. FIG. 8 is an enlarged view of D portion surrounded by a dotted line in FIG. 6. FIGS. 6 and 8 illustrate necessary components for describing a magnetic field distribution and do not illustrate other components, of components in FIG. 1.

As illustrated in FIG. 6, the first magnet 6 and the second magnet 7 generate a cross magnetic field whose magnetic field strength in the spacing direction, which is a predetermined direction orthogonal to the conveying direction, is within a predetermined range in the conveyance path 2. For example, at both ends of the first magnet 6 is generated a cross magnetic field whose magnetic field strength is more than or equal to a predetermined value recognized as a strong magnetic field strength. The AMR element 10 is located in a strong magnetic field strength region whose magnetic field strength in the spacing direction is within a predetermined range. The object to be detected 5 passes through the strong magnetic field strength region so as to intersect with the magnetic field in the spacing direction.

Figure 8A:
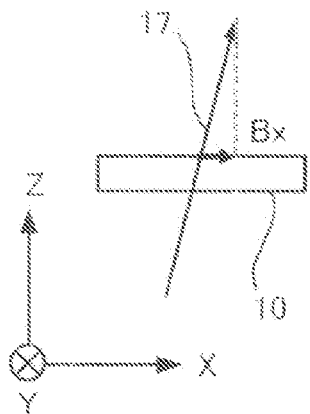
FIG. 8 is a diagram of a vector of a magnetic field line for describing a detection principle of the magnetic sensor device according to the First Embodiment.

In FIG. 6, in a cross magnetic field that is orthogonal to the conveying direction and in which the AMR element 10 is disposed, a magnetic field component in the spacing direction from the north pole of the second magnet 7 to the south pole of the first magnet 6 is the main magnetic field component of magnetic field lines 17. Since the magnetic field line 17, as illustrated in FIG. 8A, inclines a little from the spacing direction to the conveying direction, a conveying direction magnetic field component in the cross magnetic field acts as a bias magnetic field of the AMR element 10.

Figure 8B:
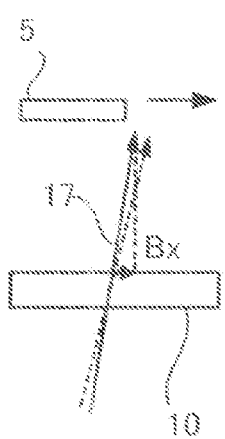
Figure 8C:
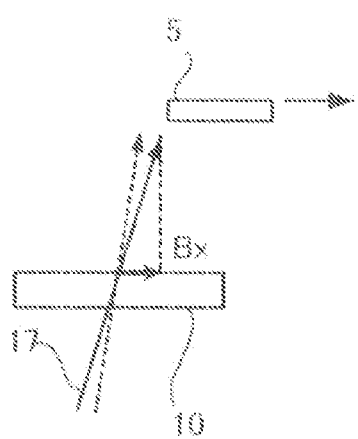

As the object to be detected 5 approaches, the magnetic field line 17 inclines toward the object to be detected 5 as illustrated in FIG. 8B, which reduces the conveying direction magnetic field component in the cross magnetic field. As the object to be detected 5 moves away, the magnetic field line 17 inclines toward the object to be detected 5 as illustrated in FIG. 8C, which increases the conveying direction magnetic field component in the cross magnetic field. The change in the conveying direction magnetic field component of the cross magnetic field changes the resistance value of the AMR element 10 for sensing change in the conveying direction magnetic field component in the cross magnetic field, thereby detecting the object to be detected 5.

FIG. 9 is a graph illustrating change in the magnetic field strength in the conveying direction and change in the magnetic field strength in the spacing direction over a distance in the spacing direction in the conveyance path of the magnetic sensor device according to the First Embodiment. In FIG. 9, the horizontal axis indicates a distance in the spacing direction, Z (unit: mm), which is the distance from the second magnet 7, and the vertical axis indicates the magnetic field strength in the conveying direction and the magnetic field strength in the spacing direction (unit: mT). FIG. 10 is a graph illustrating the relationship between the magnetic field applied on the AMR element and the resistance change rate. In FIG. 10, the horizontal axis indicates applied magnetic field (unit: mT), and the vertical axis indicates a resistance change rate (unit: %). In FIG. 6, each of the first magnet 6 and the second magnet 7 has a thickness of A=5 mm in the conveying direction and a thickness of B=10 mm in the spacing direction; and the clearance between the first magnet 6 and the second magnet 7 is G=5 mm. Neodymium sintered magnets are used as the first magnet 6 and the second magnet 7. Then, at the point apart by a distance C=2.7 mm in the conveying direction from the center of the first magnet 6 were calculated change in the magnetic field strength Bx in the conveying direction and change in the magnetic field strength Bz in the clearance direction, over a distance in the spacing direction. In FIG. 9, the magnetic field strength Bx is indicated by a solid line; the magnetic field strength Bz is indicated by a dotted line.

At the center (Z=2.5 mm=G/2) of clearance G between the first magnet 6 and the second magnet 7, the magnetic field strength Bx is 0. The saturated magnetic field strength of the AMR element 10 is 5 mT as indicated by a solid line in FIG. 10, and Bx becomes 5 mT near Z=2.65 mm, as illustrated in FIG. 9. Assume that the position of the AMR element 10 is closer to the first magnet 6 by α than the center of the clearance G between the first magnet 6 and the second magnet 7. If α is set to be 0<α<0.15 mm, output from the AMR element 10 is never saturated and a suitable bias magnetic field is applied on the AMR element 10. The most preferable is a state where a bias magnetic field having about a magnetic field strength of Bx=2.5 mT is applied so that the sensitivity gradient of the AMR element 10 is the largest, and if α is set to be near α=0.08 mm, the highest output is obtained.

When the magnetic pattern of the object to be detected 5 reaches the resistors 102a, 102b, change in the magnetic field detected by the AMR element 10 is proportional to the magnetic field around the object to be detected 5 (a magnetic field applied on the object to be detected 5). In order to increase output from the AMR element 10, a stronger magnetic field needs to be applied on the object to be detected 5. In the magnetic sensor device according to the First Embodiment, if the distance between the object to be detected 5 and the AMR element 10 is short, for example, if the object to be detected 5 is near Z=3 mm, the magnetic field applied on the object to be detected 5 is Bz=around 300 mT as illustrated in FIG. 9. If the distance between the object to be detected 5 and the AMR element 10 is longer and the object to be detected 5 is near Z=4 mm, Bz=around 370 mT. Even if the AMR element 10 and the object to be detected 5 are further apart from each other, detection sensitivity above a certain level is maintained.

If the object to be detected 5 passes through the point of Z=4 mm, the distance between the AMR element 10 and the object to be detected 5 is about 1.5 mm as described above and therefore the AMR element 10 and the object to be detected 5 are close to each other. A method to mount the AMR element 10 will be described with reference to FIGS. 3 and 4 in which the AMR element 10 is protected without being in contact with the object to be detected 5.

The AMR element 10 has a thickness of around 0.5 mm, and the resistors 102a, 102b are formed on the surface of the AMR element 10. The AMR element 10 is bonded to the surface of the metal carrier 191 having a thickness of 2.02 mm in such a way that the resistors 102a, 102b are located at the point of Z=G/2+α=2.52 mm.

The second layer board 92 has a thickness of 0.5 mm. The electrodes 111a to 111c of the second layer board 92 are connected via the metal wires 12 to the electrodes 101a to 101c of the AMR element 10. By making the second layer board 92 have the same thickness as that of the AMR element 10, the loop height of the metal wires 12 is minimized.

The thickness of the first layer board 91 is made to be about 0.3 mm similar to the loop height of the metal wires 12. The resin 13 that is epoxy with a low viscosity is applied to the hole 91a of the first layer board and the hole 92a of the second layer board so as not to overflow from the surface of the first layer board 91, thereby protecting the AMR element 10 and metal wires 12. The electrodes 111a to 111c of the second layer board 92 are connected via the transmission line 11 to the connection pads 112a to 112c provided on the back surface of the multilayer board 9, and are connected via the connection pads 112a to 112c to the power supply voltage Vcc, processing circuit 15 and the like. This implementation protects the AMR element 10, and secures a clearance of 1.2 mm between the surface of the multilayer board 9 and the object to be detected 5 without a protrusion that blocks conveyance of the object to be detected 5.

In this way, a strong magnetic field in the spacing direction is applied on the object to be detected 5, and the farther the object to be detected 5 is apart from the AMR element 10, the stronger the magnetic field is applied. Therefore, even if the AMR element 10 and the object to be detected 5 are apart from each other, the magnetic pattern of the object to be detected 5 can be detected and the detection sensitivity over a certain level can be maintained. The bias magnetic field strength in the conveying direction to be applied on the AMR element 10 does not change so much depending on the position in the spacing direction, thereby improving assembly accuracy. Further, since the first magnet 6 and the second magnet 7 are disposed so as to face each other, a stable magnetic path is formed, thereby stably detecting the magnetic pattern of the object to be detected 5 without being susceptible to an external magnetic body.

FIG. 11 is a top view of an AMR element having meander-shaped resistors in the magnetic sensor device according to the First Embodiment. Instead of the rectangular resistors 102a, 102b, the AMR element 10 may have meander-shaped resistors whose long sides extend in the reading width direction, as illustrated in FIG. 11. Meander-shaped means a folded pattern as illustrated in FIG. 11. Compared with the rectangular resistors 102a, 102b, resistance values of the meander-shaped resistors 102a 102b increase to high resistance values, thereby improving sensitivity of the AMR element 10 to detect change in the magnetic field which, in turn, improves detection sensitivity of the magnetic sensor device.

In the First Embodiment, the AMR element 10 is bonded to the surface of the metal carrier 191 in the multilayer board 9. In the case where an AMR element 10 having different resistance change rate and saturated magnetic field strength is used and the AMR element 10 is close to the first magnet 6, a structure may be employed in which the AMR element 10 is bonded to the surface on the conveyance path 2 side of the first magnet 6 without the metal carrier 191.

Instead of the AMR element 10, a GMR (giant magnetoresistance effect) element or a TMR (tunnel magnetoresistance effect) element may be used.

Second Embodiment

Figure 12:
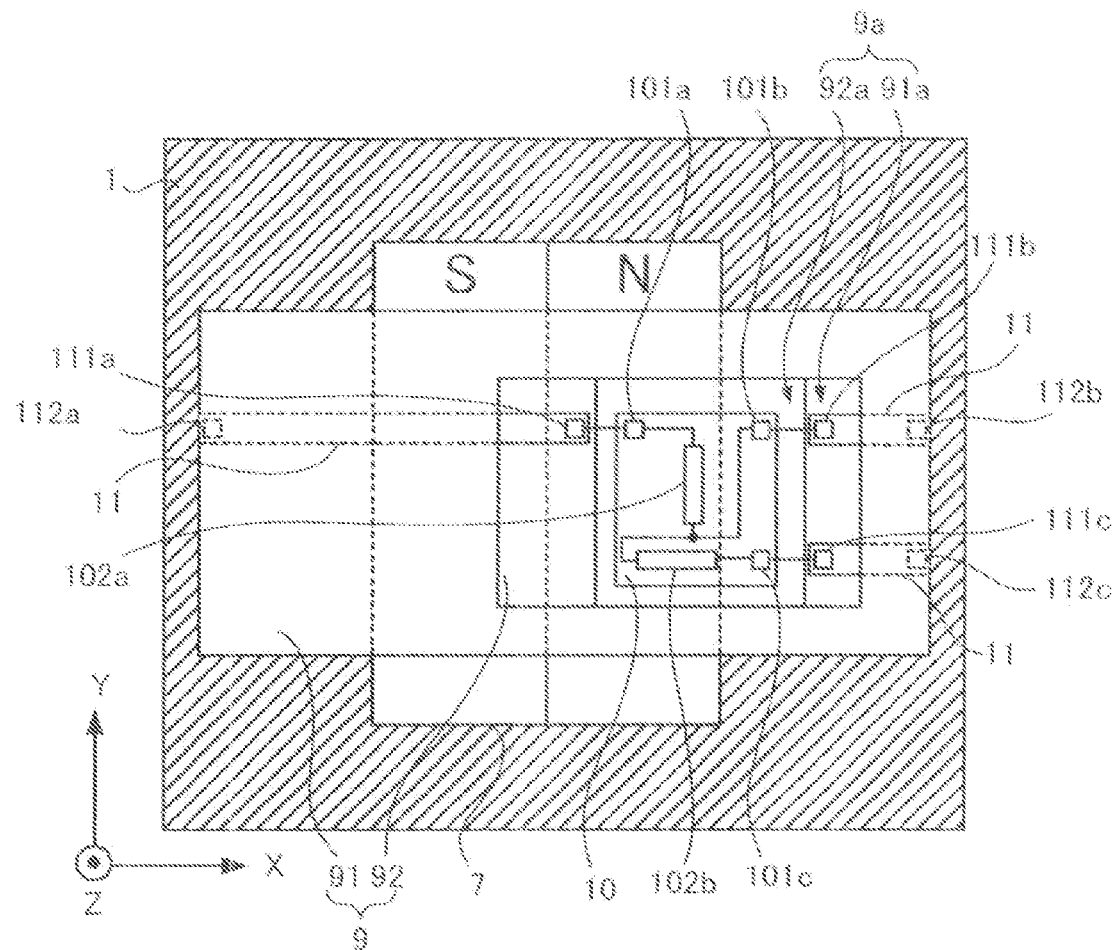
FIG. 12 is a top view of a multilayer board and an AMR element in a magnetic sensor device according to Second Embodiment of the present invention, seen from the conveyance path side.

FIG. 12 is a top view of a multilayer board and an AMR element in a magnetic sensor device according to Second Embodiment of the present invention, seen from the conveyance path side. The same components as those in FIG. 4 have the same reference signs. In FIG. 12, the resistor 102a of the AMR element 10 is disposed in such a way that the long side of the rectangular shape of the resistor 102a extends in the reading width direction; the resistor 102b is disposed in such a way that the long side of the rectangular shape of the resistor 102b extends in the conveying direction; a connection point that connects the resistor 102a and the resistor 102b in series is connected to the electrode 101b of the AMR element 10; the other end of the resistor 102a is connected to the electrode 101a; and the other end of the resistor 102b is connected to the electrode 101c.

Figure 13:
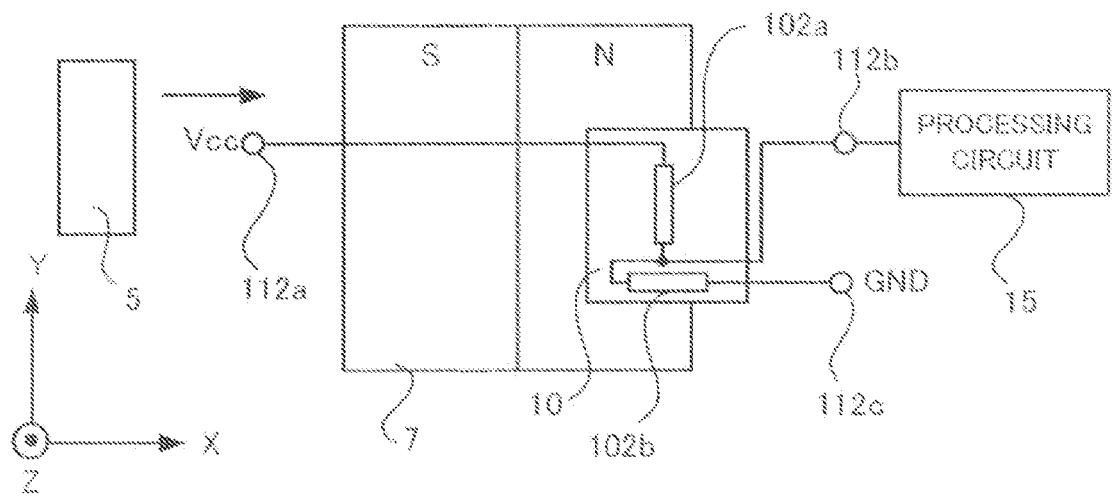
FIG. 13 is a diagram illustrating connection of the AMR element and an external circuit in the magnetic sensor device according to the Second Embodiment.

FIG. 13 is a diagram illustrating connection of the AMR element and an external circuit in the magnetic sensor device according to the Second Embodiment. The same components as those in FIG. 5 have the same reference signs. In FIGS. 12 and 13, the electrode 101a is connected via the metal wire 12 to the electrode 111a, which is connected via the connection pad 112a to the DC power supply voltage Vcc. The electrode 101b is connected via the metal wire 12 to the electrode 111b, which is connected via the connection pad 112b to the processing circuit 15 that processes signals. The electrode 101c is connected via the metal wire 12 to the electrode 111c, which is DC grounded via the connection pad 112c.

In the magnetic sensor device according to the Second Embodiment, like the magnetic sensor device according to the First Embodiment, the spacing direction magnetic field component is the main magnetic field component of the magnetic field lines 17 in a cross magnetic field. Since the magnetic field lines 17 incline a little from the spacing direction to the conveying direction, the conveying direction magnetic field component in this magnetic field acts as a bias magnetic field of the AMR element 10. A bias magnetic field Bx is applied on the resistor 102a. However, since Bx is not the sensing direction for the resistor 102b, the bias magnetic field is not applied on the resistor 102b. In this state, when the object to be detected 5 is conveyed in the conveying direction and the magnetic pattern of the object to be detected 5 reaches the resistor 102a, the magnetic field Bx near the resistor 102a changes, thereby changing the resistance value of the resistor 102a. Meanwhile, since change in the magnetic field Bx near the resistor 102b is not sensed by the resistor 102b, the resistance value of the resistor 102b is always fixed. Accordingly, the magnetic pattern is able to be detected with only change in the magnetic field sensed by the resistor 102a.

Figure 14:
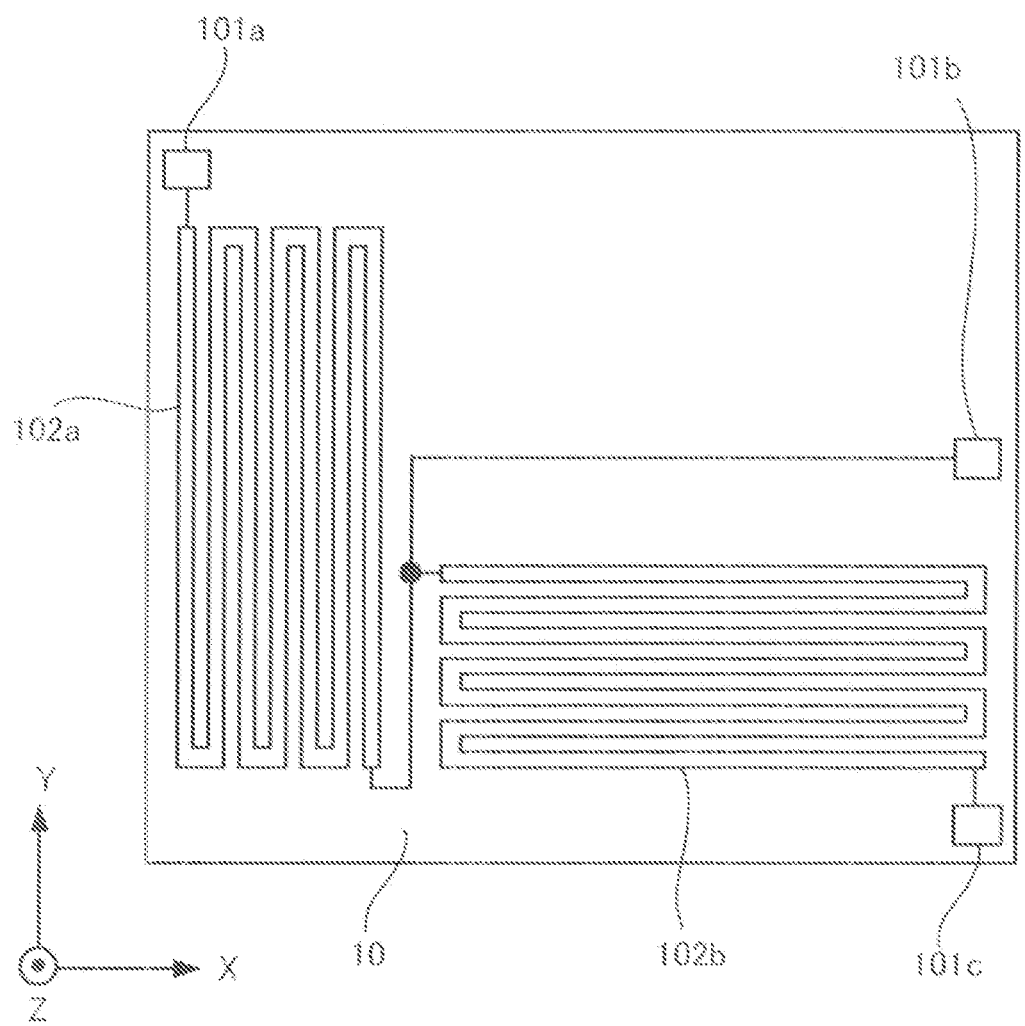
FIG. 14 is a top view of an AMR element having meander-shaped resistors in the magnetic sensor device according to the Second Embodiment.

FIG. 14 is a top view of an AMR element having meander-shaped resistors in the magnetic sensor device according to the Second Embodiment. The resistors 102a, 102b of the AMR element 10 may be meander-shaped, the resistor 102a may be disposed in such a way that its long side extends in the reading width direction, and the resistor 102b may be disposed in such a way that its long side extends in the conveying direction, as illustrated in FIG. 14. In this case, resistance values of the resistors 102a, 102b increase to high resistance values, compared with rectangular resistors, thereby improving sensitivity of the AMR element 10 to detect change in the magnetic field which, in turn, improves the detection sensitivity of the magnetic sensor device.

Third Embodiment

Figure 15:
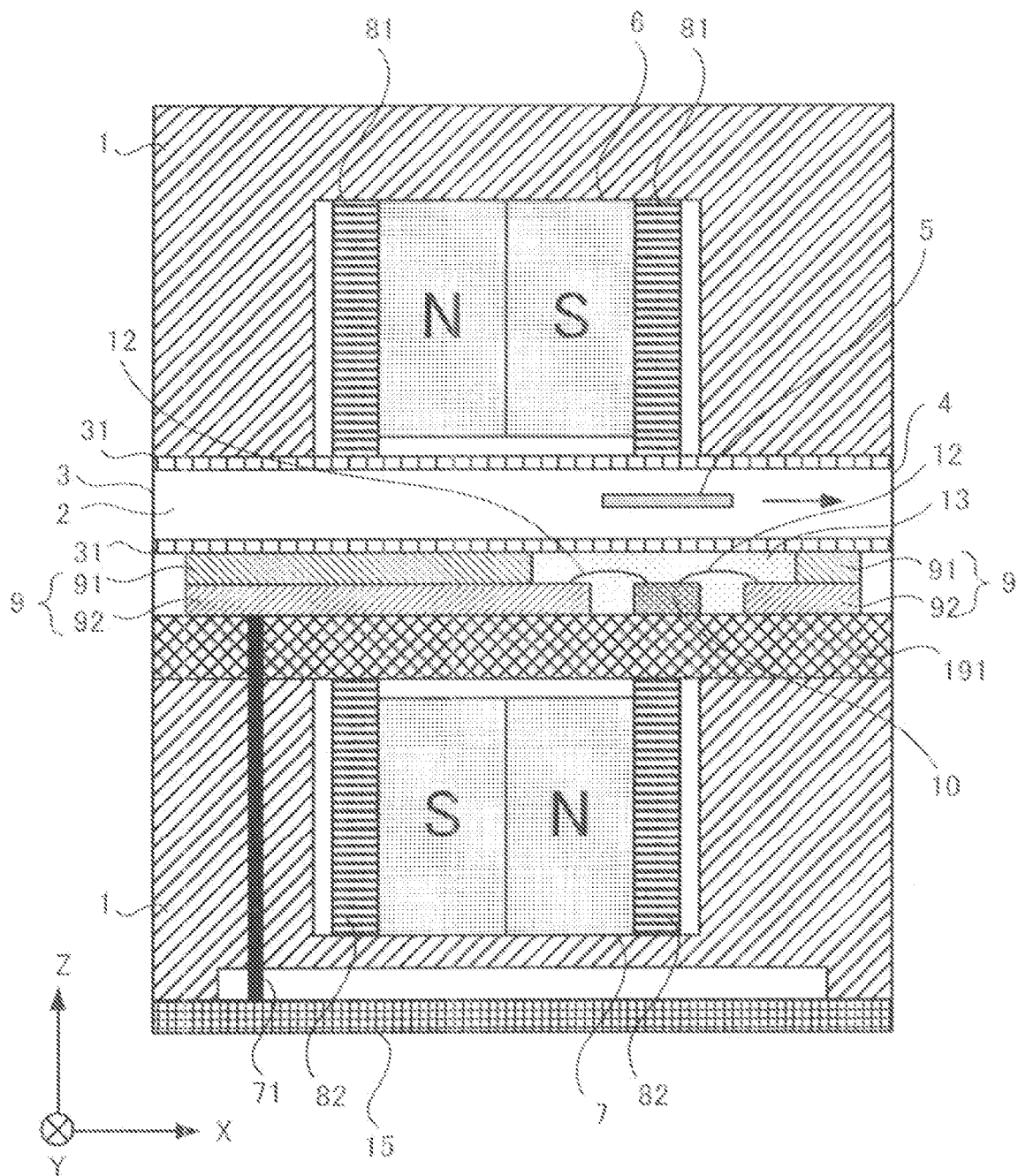
FIG. 15 is a cross-sectional view along the conveying direction of a magnetic sensor device according to Third Embodiment of the present invention.

FIG. 15 is a cross-sectional view along the conveying direction of a magnetic sensor device according to Third Embodiment of the present invention. The same components as those in FIG. 1 have the same reference signs. The magnetic sensor device according to the Third Embodiment further includes: yokes for the first magnet 81 that are a pair of magnetic bodies, each being in contact with each of side surfaces orthogonal to the conveying direction, of side surfaces of the first magnet 6; and the yokes for the second magnet 82 that are a pair of magnetic bodies, each being in contact with each of side surfaces orthogonal to the conveying direction, of side surfaces of the second magnet 7, in addition to the configuration of the magnetic sensor device according to the First Embodiment in FIG. 1.

Figure 16:
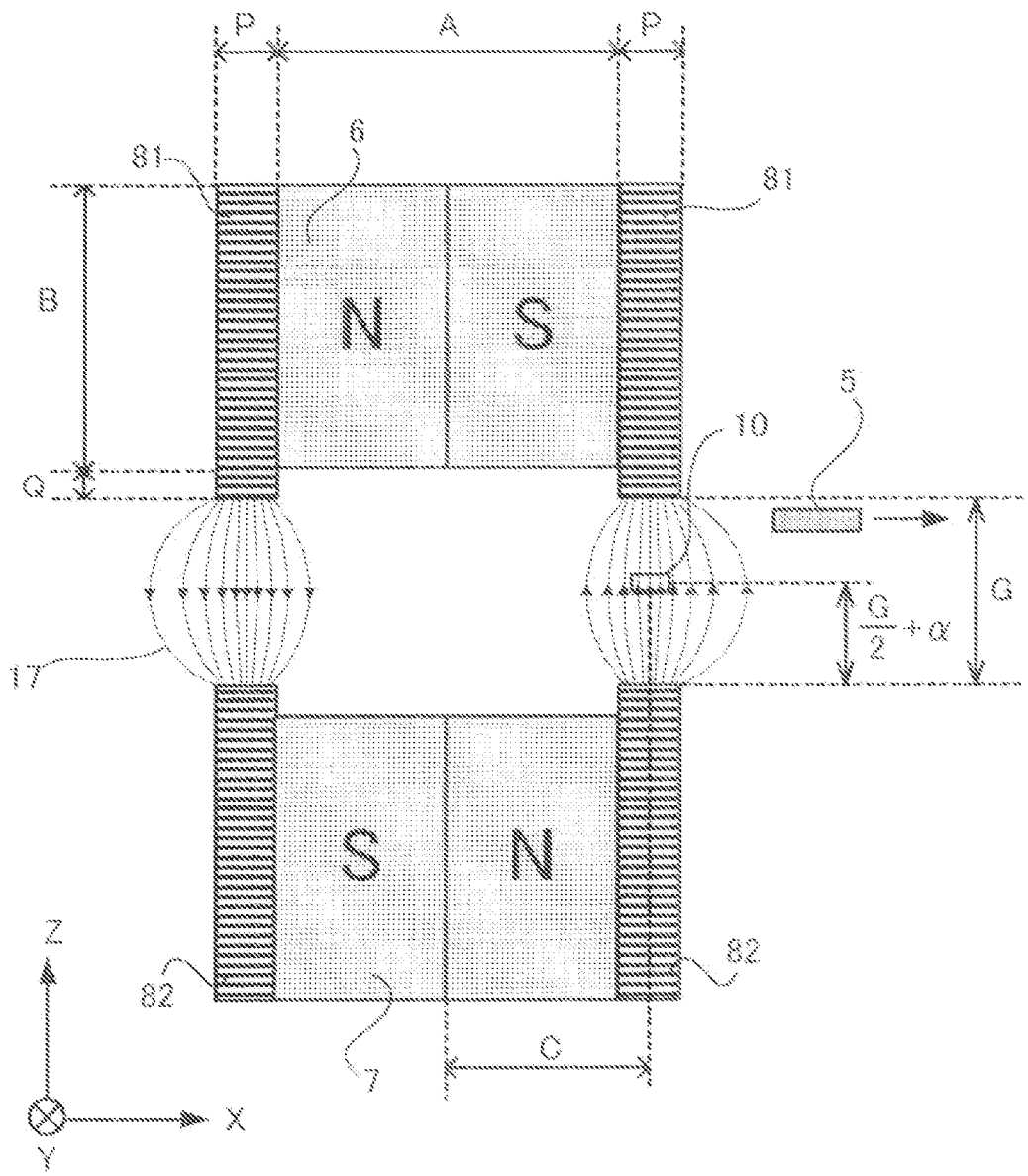
FIG. 16 is a diagram illustrating a magnetic field distribution in the spacing direction, the magnetic field distribution being generated by yokes for a first magnet and yokes for a second magnet in a conveyance path of the magnetic sensor device according to the Third Embodiment.

FIG. 16 is a diagram illustrating a magnetic field distribution in the spacing direction, the magnetic field distribution being generated by the yokes for the first magnet and the yokes for the second magnet in a conveyance path of the magnetic sensor device according to the Third Embodiment. FIG. 16 illustrates components necessary for describing the magnetic field distribution and does not illustrate other components, of components in FIG. 15.

As illustrated in FIG. 16, the AMR element 10 is located in a strong magnetic field strength region whose magnetic field strength in the spacing direction is within a predetermined range. The object to be detected 5 passes through the strong magnetic field strength region so as to intersect with the magnetic field in the spacing direction.

The yokes for the first magnet 81 are made of plate-like soft magnetic bodies, each having a thickness of P in the conveying direction (a thickness in the spacing direction of the first magnet 6 and the second magnet 7 B>P). The yokes for the first magnet 81 are mounted to both sides of the first magnet 6 by adhesion, casting, a magnetic attraction, or the like in such a way that the lower ends in the spacing direction of the yokes for the first magnet 81 and the lower end in the spacing direction of the first magnet 6 are aligned with each other or in such a way that lower ends in the spacing direction of the yokes for the first magnet 81 are located lower by a predetermined thickness than a lower end in the spacing direction of the first magnet 6. The yokes for the second magnet 82 are made of plate-like soft magnetic bodies, each having a thickness of P in the conveying direction. The yokes for the second magnet 82 are mounted to both sides of the second magnet 7 by adhesion, casting, a magnetic attraction, or the like in such a way that upper ends in the spacing direction of the yokes for the second magnet 82 and an upper end in the spacing direction of the second magnet 7 are aligned with each other or in such a way that upper ends in the spacing direction of the yokes for the second magnet 82 are located higher by a predetermined thickness than an upper end in the spacing direction of the first magnet 7.

In this configuration, the magnetic field lines 17 emitted from the side surface of the first magnet 6 and the side surface of the second magnet 7 are collected by the yoke for the first magnet 81 and the yoke for the second magnet 82, respectively, each of the yokes for the first magnet 81 and yokes for the second magnet 82 having a thickness P in the conveying direction. As illustrated in FIG. 16, the magnetic field lines 17 are emitted from the end of the yoke for the first magnet 81 that is in contact with the north pole of the first magnet 6, and arc toward the end of the yoke for the second magnet 82 that is in contact with the south pole of the second magnet 7; and the magnetic field lines 17 are emitted from the end of the yoke for the second magnet 82 that is in contact with the north pole of the second magnet 7, and arc toward the end of the yoke for the first magnet 81 that is in contact with the south pole of the first magnet 6. The magnetic sensor device according to the Third Embodiment is able to detect the object to be detected 5 such as paper money, in the same principle as that used in the magnetic sensor device according to the First Embodiment in FIG. 8. By providing the yokes for the first magnet 81 and yokes for the second magnet 82, a stronger magnetic field is applied on the object to be detected 5 and the assembly accuracy is improved, compared with the case in which only the first magnet 6 and the second magnet 7 face each other.

Figure 17:
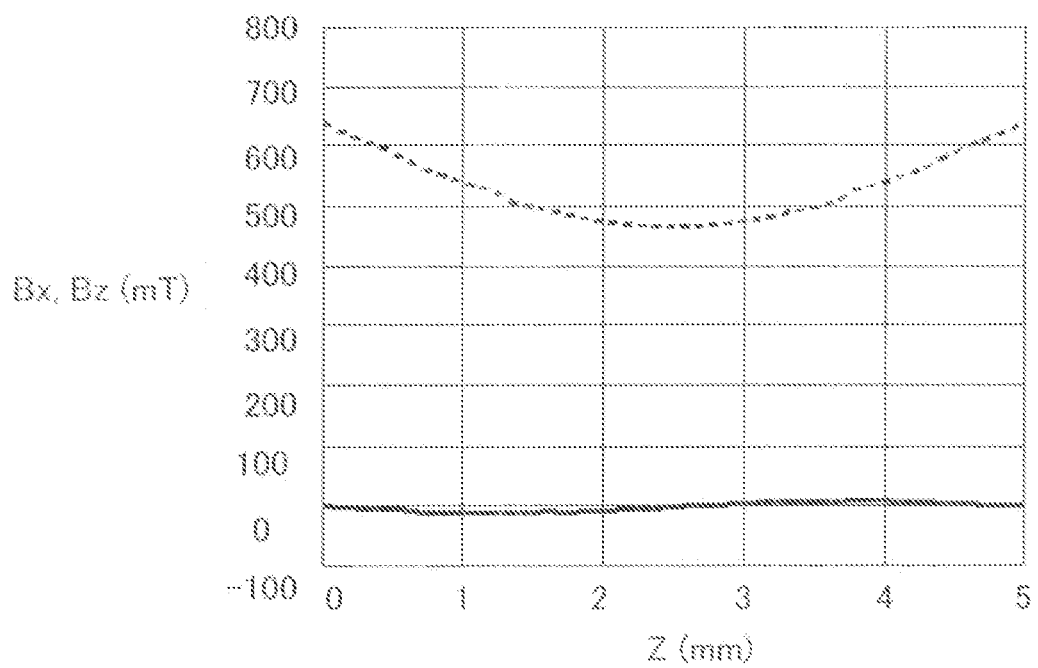
FIG. 17 is a graph illustrating change in a magnetic field strength in the conveying direction and change in a magnetic field strength in the spacing direction over a distance in the spacing direction in the conveyance path of the magnetic sensor device according to the Third Embodiment.

FIG. 17 is a graph illustrating change in the magnetic field strength in the conveying direction and change in the magnetic field strength in the spacing direction over a distance in the spacing direction in the conveyance path of the magnetic sensor device according to the Third Embodiment. In FIG. 17, the horizontal axis indicates a distance in the spacing direction, Z (unit: mm), which is the distance from the yoke for the second magnet 82; and the vertical axis indicates a magnetic field strength in the conveying direction and a magnetic field strength in the spacing direction (unit: mT). In FIG. 16, each of the first magnet 6 and the second magnet 7 has a thickness of A=5 mm in the conveying direction and a thickness of B=10 mm in the spacing direction; each of the yokes for the first magnet 81 and the yokes for the second magnet 82 has a thickness of P=3 mm in the conveying direction. The lower ends in the spacing direction of the yokes for the first magnet 81 are located lower by Q=1 mm than the lower end in the spacing direction of the first magnet 6, and the upper ends in the spacing direction of the yokes for the second magnet 82 are located higher by Q=1 mm than the upper end in the spacing direction of the second magnet 7. The clearance between the yokes for the first magnet 81 and the yokes for the second magnet 82 is G=5 mm Neodymium sintered magnets are used as the first magnet 6 and the second magnet 7. Then, at the position apart by a distance C=4.0 mm in the conveying direction from the center of the first magnet 6 were calculated change in the magnetic field strength in the conveying direction Bx and change in the magnetic field strength in the spacing direction Bz, over a distance in the spacing direction. The magnetic field strength component Bx is indicated by a solid line, and the magnetic field strength component Bz is indicated by a dotted line.

The magnetic field strength Bx is 0 at the center (Z=2.5 mm=G/2) of clearance G between the yoke for the first magnet 81 and the yoke for the second magnet 82. The saturated magnetic field strength of the AMR element 10 is 5 mT as illustrated by a solid line in FIG. 10, and Bx is 5 mT near Z=3.0 mm, as illustrated in FIG. 17. Assume that the position of the AMR element 10 is the position that is closer by a to the yoke for the first magnet 81 than the center of clearance G between the yoke for the first magnet 81 and the yoke for the second magnet 82. If α is set to be 0<α<0.5 mm, output from the AMR element 10 is not saturated and a suitable bias magnetic field is applied on the AMR element 10, which shows that the assembly accuracy is significantly improved, compared with the assembly accuracy of the magnetic sensor device according to the First Embodiment (0<α<0.15 mm). The most preferable is the state in which a bias magnetic field having a magnetic field strength of Bx=around 2.5 mT is applied so that the sensitivity gradient of the AMR element 10 is the largest, and if α is set to be near α=0.25 mm, the highest output is obtained.

When the magnetic pattern of the object to be detected 5 reaches the resistors 102a, 102b, change in the magnetic field detected by the AMR element 10 is proportional to the magnetic field around the object to be detected 5 (the magnetic field applied on the object to be detected 5). In order to increase output from the AMR element 10, a stronger magnetic field needs to be applied on the object to be detected 5. In the magnetic sensor device according to the Second Embodiment, if the distance between the object to be detected 5 and the AMR element 10 is short, for example, if the object to be detected 5 is near Z=3 mm, the magnetic field applied to the object to be detected 5 is Bz=around 480 mT, illustrated in FIG. 17. If the distance between the object to be detected 5 and the AMR element 10 is longer and the object to be detected 5 is near Z=4 mm, Bz=around 540 mT. Even if the AMR element 10 and the object to be detected 5 are further apart from each other, detection sensitivity above a certain level is maintained, which is significantly improved, compared with the magnetic field applied on the object to be detected 5 in the magnetic sensor device according to the First Embodiment. As a result, a stable output is obtained.

By attaching the yokes for the first magnet 81 and the yokes for the second magnet 82 to both sides of the first magnet 6 and both sides of the second magnet 7, respectively, variations of magnetic forces in the reading width direction of the first magnet 6 and the second magnet 7 can be evened out. Particularly in the case of a line-type magnetic sensor, variations of bias magnetic fields among respective channels are reduced which, in turn, reduces variations of outputs among lines, thereby increasing the yield and reducing cost.

Fourth Embodiment

Figure 18:
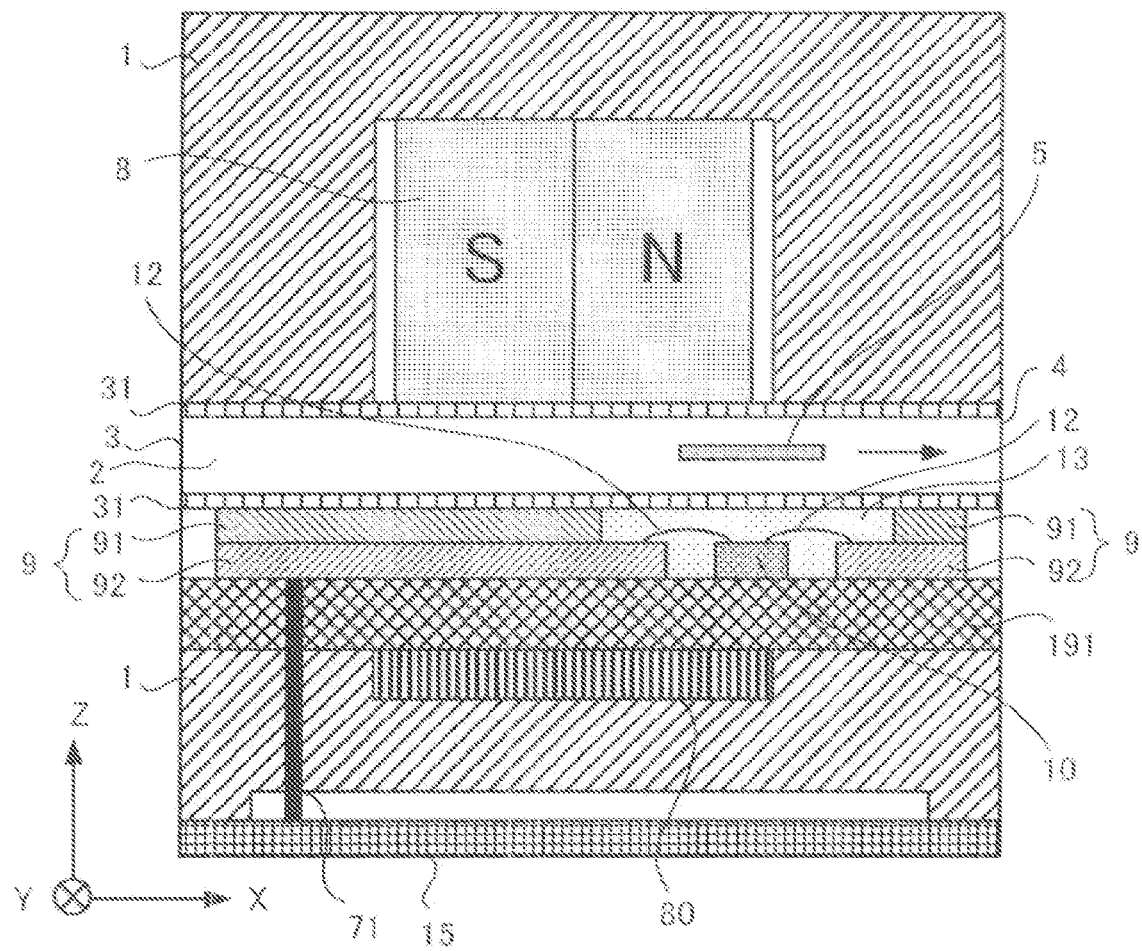
FIG. 18 is a cross-sectional view along the conveying direction of a magnetic sensor device according to Fourth Embodiment of the present invention.

FIG. 18 is a cross-sectional view along the conveying direction of a magnetic sensor device according to Fourth Embodiment of the present invention. The same components as those in FIG. 1 have the same reference signs. In the magnetic sensor device according to the Fourth Embodiment, a magnet 8 and a magnetic body 80 face each other, unlike the magnetic sensor device according to the First Embodiment in FIG. 1. As the magnetic body 80, a soft magnetic body such as iron is used.

Figure 19:
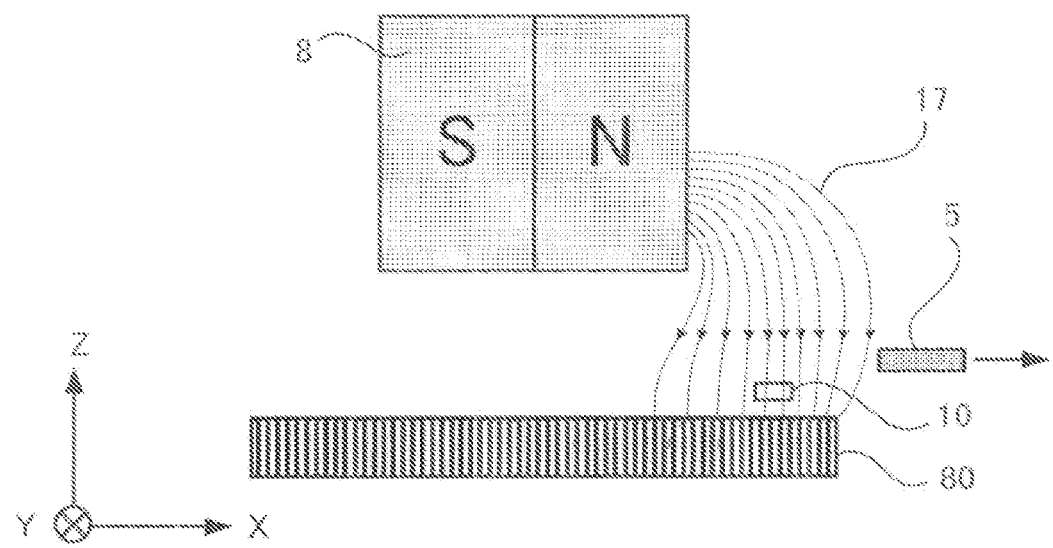
FIG. 19 is a diagram illustrating a magnetic field distribution generated by a magnet and a magnetic body in a conveyance path of the magnetic sensor device according to the Fourth Embodiment.

FIG. 19 is a diagram illustrating a magnetic field distribution generated by the magnet and the magnetic body in a conveyance path of the magnetic sensor device according to the Fourth Embodiment. FIG. 19 illustrates components necessary for describing the magnetic field distribution, and does not illustrate other components, of components in FIG. 18. In FIG. 19, the magnetic field strength in the spacing direction generated by the magnet 8 and the magnetic body 80 that face each other over a distance in the conveying direction has a distribution in which the magnetic field strength is 0 near the center in the conveying direction of the magnet 8 and the absolute value of the magnetic field strength increases toward both ends of the magnet 8, like in FIG. 7.

As illustrated in FIG. 19, the AMR element 10 is located in a strong magnetic field strength region whose magnetic field strength in the spacing direction is within a predetermined range. The object to be detected 5 passes through the strong magnetic field strength region so as to intersect with the magnetic field in the spacing direction.

In FIG. 19, in a cross magnetic field that is orthogonal to the conveying direction and in which the AMR element 10 is disposed, a spacing direction magnetic field component from the north pole of the magnet 8 to the magnetic body 80 is the main magnetic field component of the magnetic field lines 17. The magnetic sensor device according to the Fourth Embodiment is also able to detect the object to be detected 5 such as paper money in the same principle as that used by the magnetic sensor device according to the First Embodiment in FIG. 8.

In the magnetic sensor device according to the Fourth Embodiment, the bias magnet is disposed on only one side and a soft magnetic body such as cheap iron is disposed at the other side, thereby reducing production cost of the magnetic sensor device.

Fifth Embodiment

Figure 20:
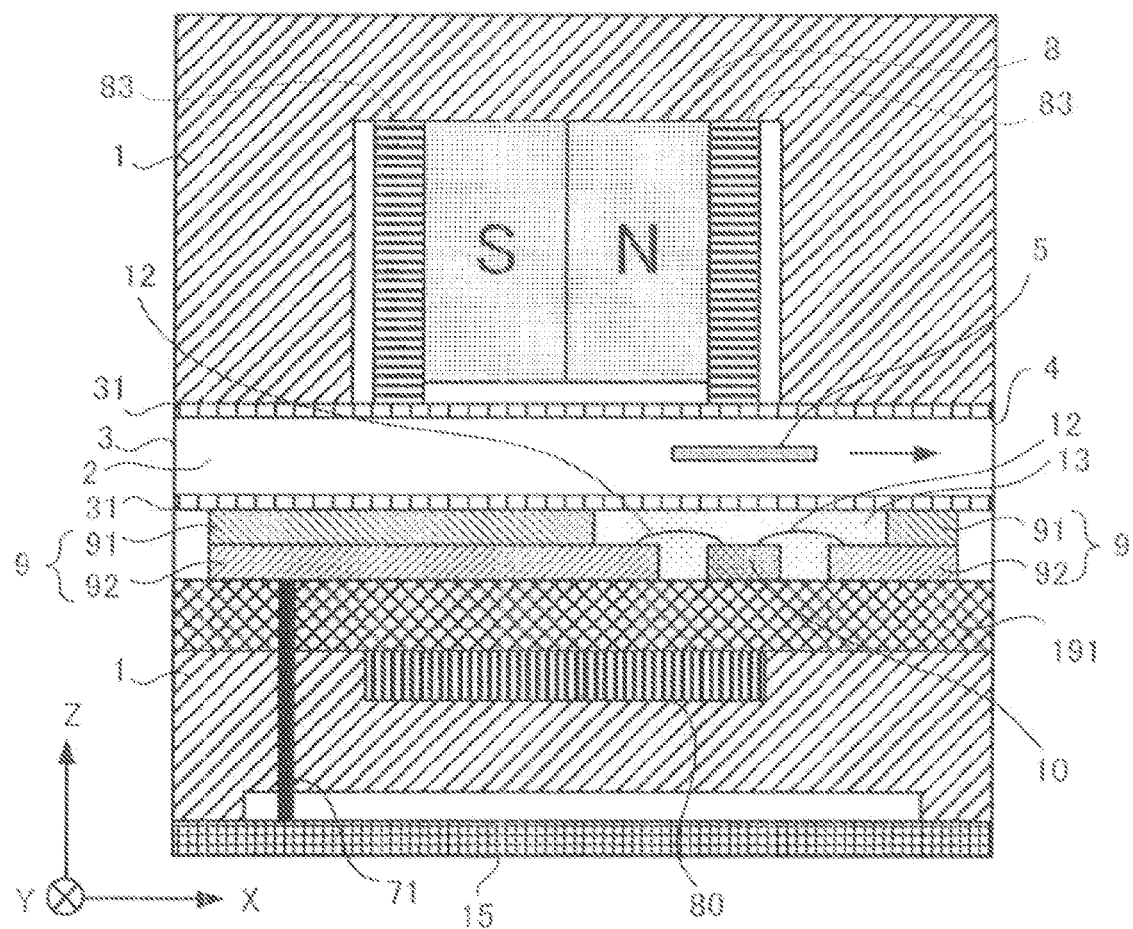
FIG. 20 is a cross-sectional view along the conveying direction of a magnetic sensor device according to Fifth Embodiment of the present invention.

FIG. 20 is a cross-sectional view along the conveying direction of a magnetic sensor device according to Fifth Embodiment of the present invention. The magnetic sensor device according to the Fifth Embodiment includes yokes for a magnet 83 that are a pair of magnetic bodies, each being in contact with each of side surfaces orthogonal to the conveying direction, of side surfaces of the magnet 8, in addition to the configuration of the magnetic sensor device according to the Fourth Embodiment in FIG. 18. The shapes of the yokes are the same as those of the yokes for the first magnet 81 of the magnetic sensor device according to the Third Embodiment. The same components as those in FIG. 18 have the same reference signs.

Figure 21:
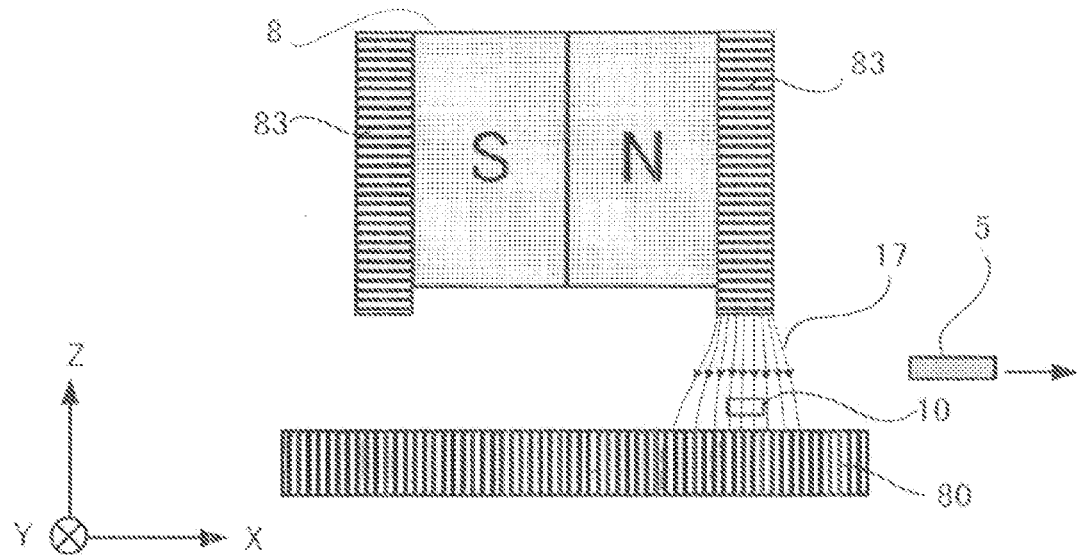
FIG. 21 is a diagram illustrating a magnetic field distribution generated by a yoke for a magnet and a magnetic body in a conveyance path of the magnetic sensor device according to the Fifth Embodiment.

FIG. 21 is a diagram illustrating a magnetic field distribution generated by the yoke for the magnet and the magnetic body in a conveyance path of the magnetic sensor device according to the Fifth Embodiment. FIG. 21 illustrates components necessary for describing the magnetic field distribution and does not illustrate other components, of components in FIG. 20.

As illustrated in FIG. 21, the AMR element 10 is located in a strong magnetic field strength region whose magnetic field strength in the spacing direction is within a predetermined range. The object to be detected 5 passes through the strong magnetic field strength region so as to intersect with the magnetic field in the spacing direction.

In FIG. 21, in a cross magnetic field that is orthogonal to the conveying direction and in which the AMR element 10 is disposed, a spacing direction magnetic field component from the yoke for the magnet 83 that is in contact with the north pole of the magnet 8 to the magnetic body 80 is the main magnetic field component of the magnetic field lines 17. The magnetic sensor device according to the Fifth Embodiment is also able to detect the object to be detected 5 such as paper money in the same principle as that used by the magnetic sensor device according to the First Embodiment in FIG. 8.

In this configuration, the magnetic field lines 17 emitted from the side surface of the magnet 8 are collected by the yoke for the magnet 83, the yoke for the magnet 83 having a thickness of P in the conveying direction, and then the magnetic field lines 17 are emitted from the end of the yoke for the magnet 83 that is in contact with the north pole of the magnet 8 and arc toward the magnetic body 80, as illustrated in FIG. 21. By providing the yokes for the magnet 83, a stronger magnetic field is applied on the object to be detected 5 and the assembly accuracy is improved, compared with the magnetic sensor device according to the Fourth Embodiment.

In the magnetic sensor device according to the Fifth Embodiment, the bias magnet is disposed at only one side and a soft magnetic body such as cheap iron is disposed at the other side, which reduces production cost of the magnetic sensor device.

Sixth Embodiment

Figure 22:
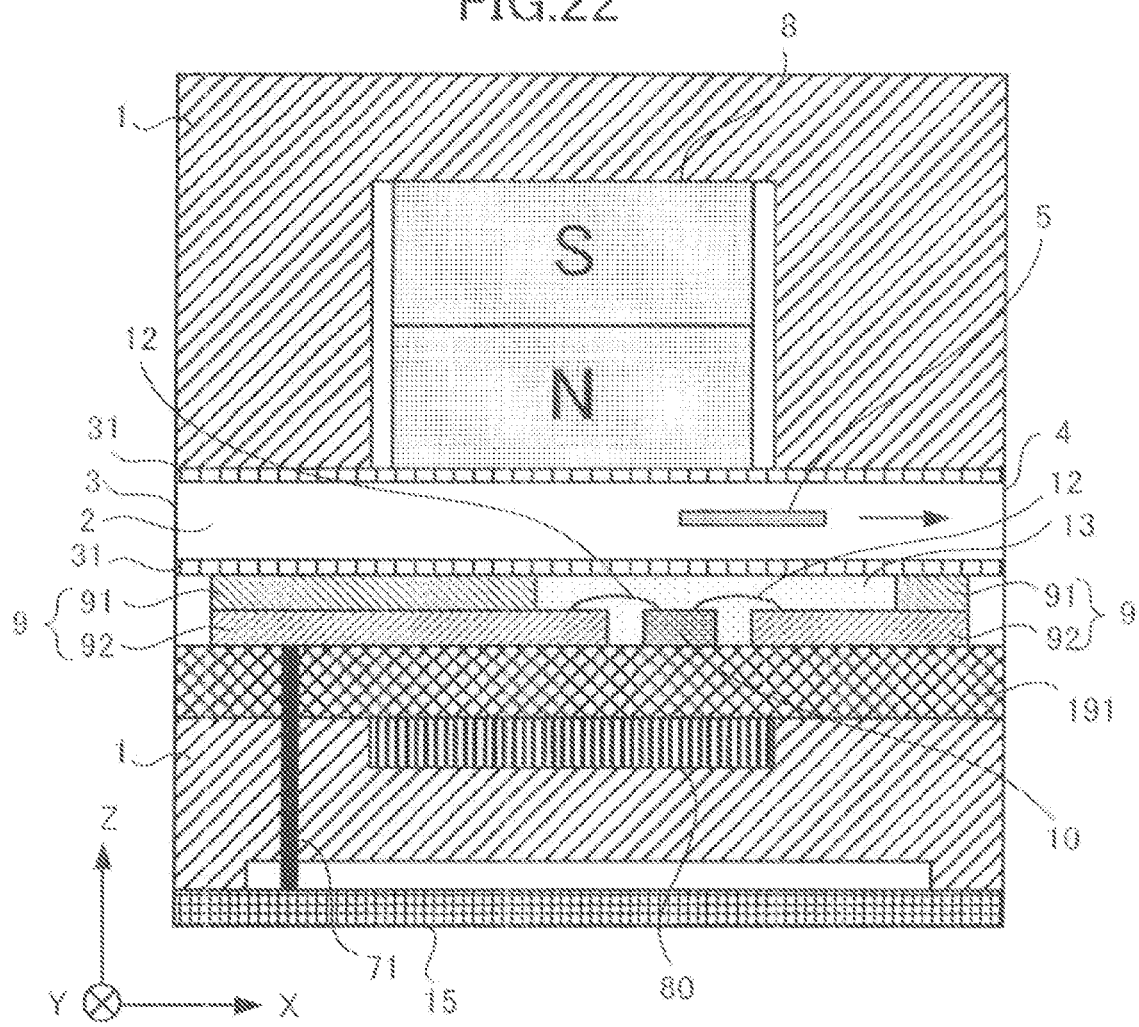
FIG. 22 is a cross-sectional view along the conveying direction of a magnetic sensor device according to Sixth Embodiment of the present invention.

FIG. 22 is a cross-sectional view along the conveying direction of a magnetic sensor device according to Sixth Embodiment of the present invention. In the magnetic sensor device according to the Sixth Embodiment, orientation of the magnet 8 of the magnetic sensor device according to the Fourth Embodiment in FIG. 18 is changed so that either one of the poles of the magnet 8 faces the magnetic body 80. The same components as those in FIG. 18 have the same reference signs.

Figure 23:
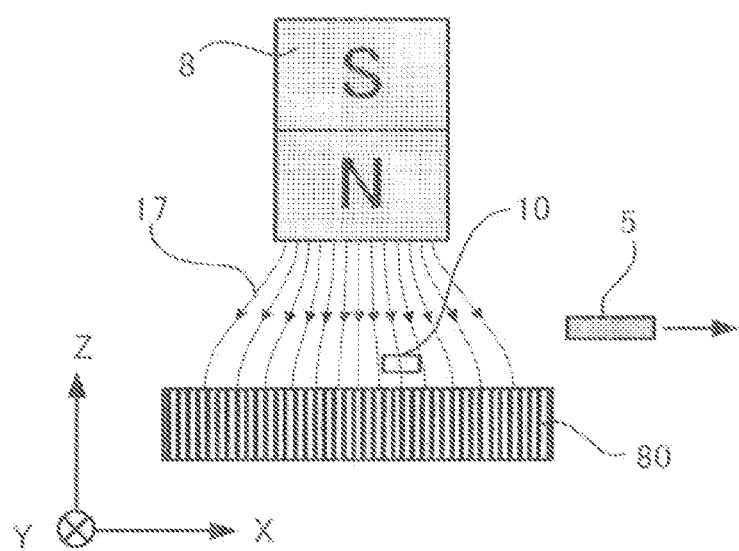
FIG. 23 is a diagram illustrating a magnetic field distribution generated by a magnet and a magnetic body in a conveyance path of the magnetic sensor device according to the Sixth Embodiment.

FIG. 23 is a diagram illustrating a magnetic field distribution generated by the magnet and the magnetic body in a conveyance path of the magnetic sensor device according to the Sixth Embodiment. FIG. 23 illustrates components necessary for describing the magnetic field distribution, and does not illustrate other components, of components in FIG. 22. In FIG. 23, the magnetic field strength in the spacing direction has a distribution in which the absolute value of the magnetic field strength is the maximum near the center in the conveying direction of the magnet 8 and decreases toward the both ends.

As illustrated in FIG. 23, the AMR element 10 is located in a strong magnetic field strength region whose magnetic field strength in the spacing direction is within a predetermined range. The object to be detected 5 passes through the strong magnetic field strength region so as to intersect with the magnetic field in the spacing direction.

In FIG. 23, in a cross magnetic field that is orthogonal to the conveying direction and in which the AMR element 10 is disposed, the spacing direction magnetic field component from the north pole of the magnet 8 to the magnetic body 80 is the main magnetic field component of the magnetic field lines 17. The magnetic sensor device according to the Sixth Embodiment is also able to detect the object to be detected 5 such as paper money in the same principle as that used by the magnetic sensor device according to the First Embodiment in FIG. 8.

Seventh Embodiment

Figure 24:
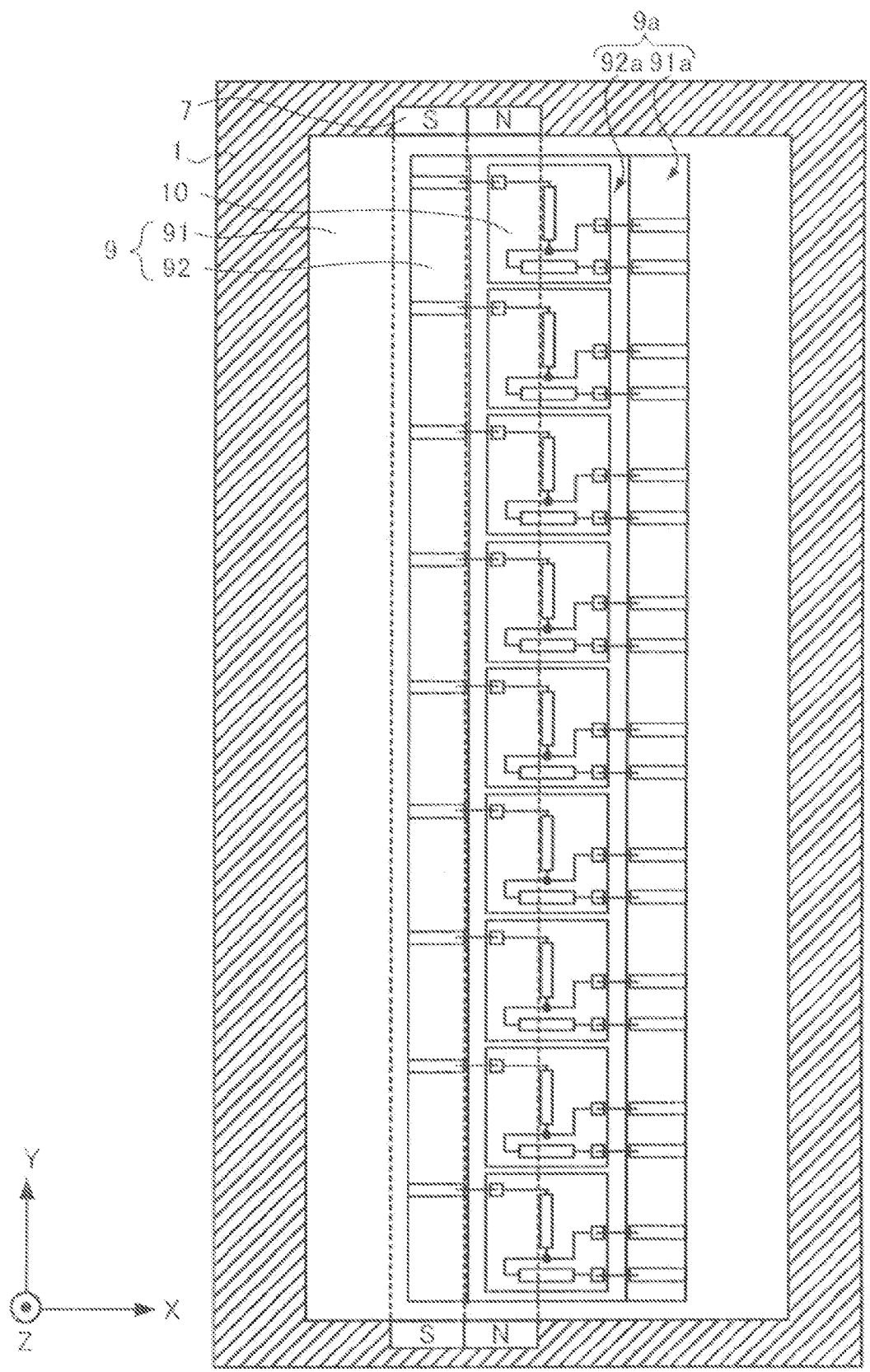
FIG. 24 is a top view of a multilayer board and an AMR element of a magnetic sensor device according to Seventh Embodiment of the present invention, seen from the conveyance path side.

FIG. 24 is a top view of a multilayer board and an AMR element of a magnetic sensor device according to Seventh Embodiment of the present invention, seen from the conveyance path side. In the magnetic sensor device according to the Seventh Embodiment, the AMR elements 10, which are the same as the AMR element 10 of the magnetic sensor device according to the Second Embodiment in FIG. 12, are arranged in an array. In FIG. 24, the same components as those in FIG. 12 have the same reference signs. In FIG. 24, a plurality of AMR elements 10 are mounted in an array in the hole 9a of the multilayer board 9, over a distance in the reading width direction. Operation is the same as that of the magnetic sensor device according to the Second Embodiment of the present invention. A method to connect the resistors 102a, 102b and the electrodes 101a to 101c of the AMR element 10 is not limited to the method in FIG. 12, but the method in FIG. 4 may be employed. Instead of the rectangular resistors 102a, 102b, the resistors may be meander-shaped, like in FIG. 11 or 14. As to arrangement of a pair of magnets located on mutually opposing sides of the conveyance path 2 or arrangement of a magnet and a magnetic body located on mutually opposing sides of the conveyance path 2, any arrangement in the first to Sixth Embodiments can be employed.

In FIG. 24, all of the AMR elements 10 are disposed in the one hole 9a, and are collectively surrounded by the multilayer board 9. Alternatively, a configuration may be employed in which the multilayer board 9 surrounds each of the AMR elements 10. Alternatively, a configuration may be employed in which the multilayer board 9 includes a plurality of holes 9a, each of the AMR elements 10 is disposed in each of the holes 9a, and the multilayer board 9 collectively surrounds the AMR elements 10.

This line-type magnetic sensor device in which a plurality of AMR elements 10 are arranged in an array enlarges the detection width.

Eighth Embodiment

Figure 25:
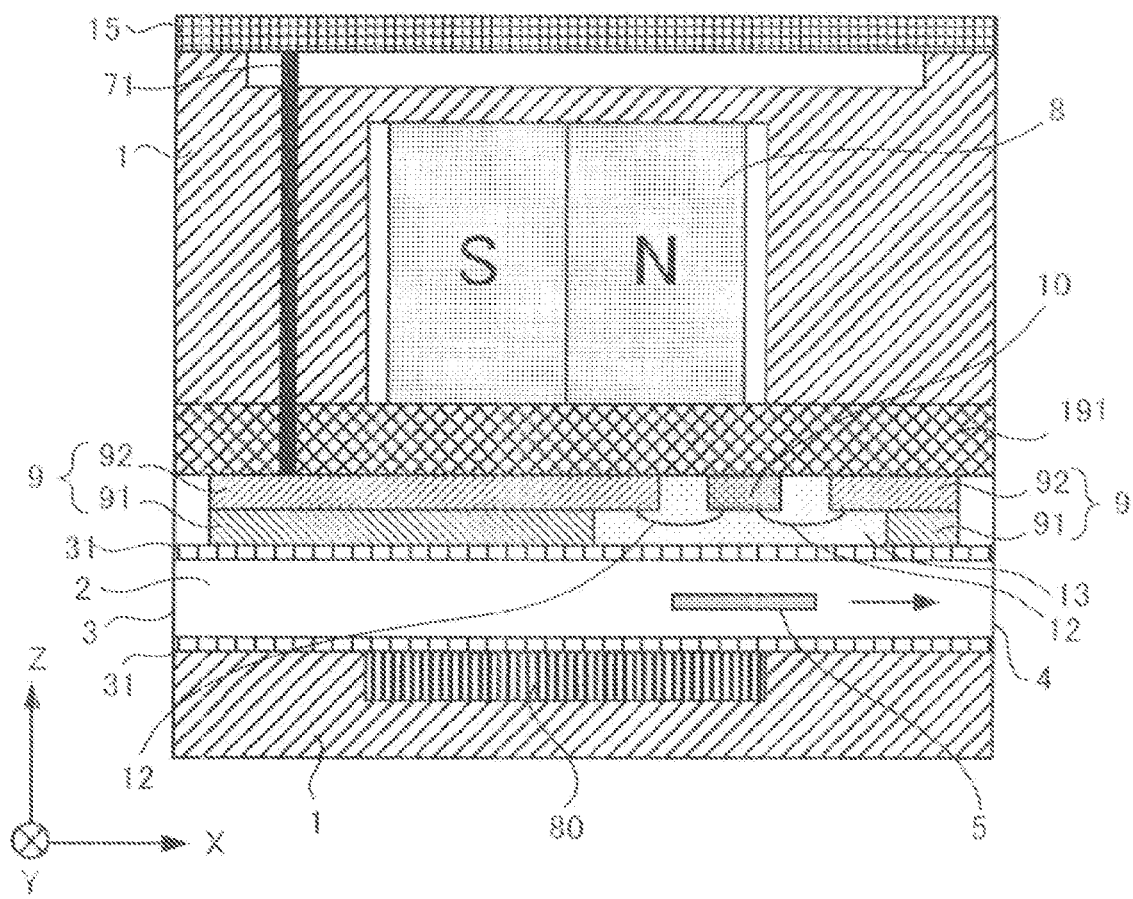
FIG. 25 is a cross-sectional view along the conveying direction of a magnetic sensor device according to Eighth Embodiment of the present invention.

FIG. 25 is a cross-sectional view along the conveying direction of a magnetic sensor device according to Eighth Embodiment of the present invention. In the magnetic sensor device according to the Eighth Embodiment, the magnet 8 and the magnetic body 80 of the magnetic sensor device according to the Fourth Embodiment in FIG. 18 are swapped and the magnetic sensor device is turned upside down. The same components as those in FIG. 18 have the same reference signs. As the magnetic body 80, a soft magnetic body such as iron is used.

Figure 26:
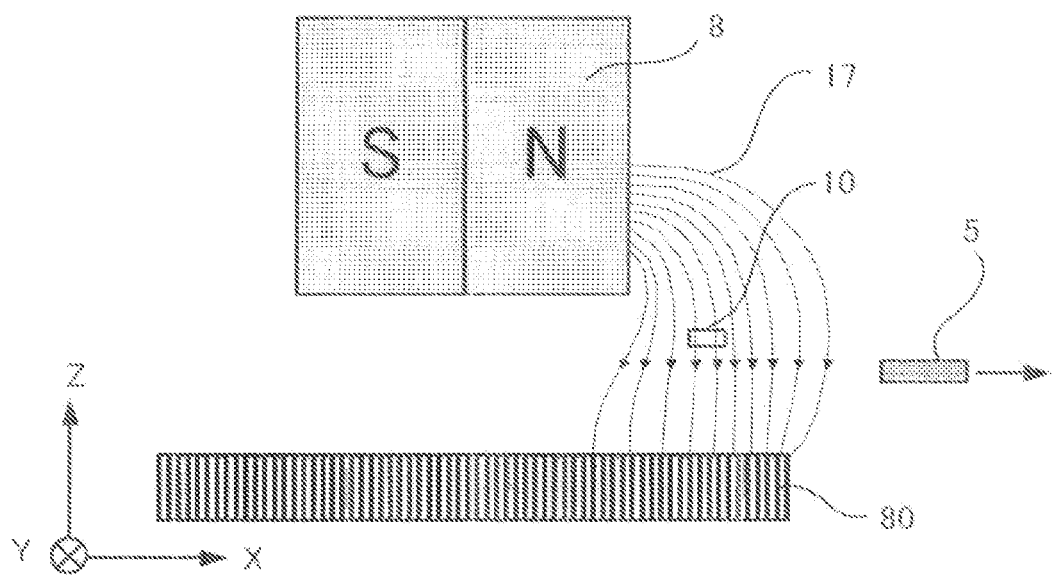
FIG. 26 is a diagram illustrating a magnetic field distribution generated by a magnet and a magnetic body in a conveyance path of the magnetic sensor device according to the Eighth Embodiment.

FIG. 26 is a diagram illustrating the magnetic field distribution generated by the magnet and the magnetic body in a conveyance path of the magnetic sensor device according to the Eighth Embodiment. FIG. 26 illustrates components necessary for describing the magnetic field distribution, and does not illustrate other components, of components in FIG. 25. In FIG. 26, the magnetic field strength in the spacing direction of the magnet 8 and the magnetic body 80 that face each other over a distance in the conveying direction has a distribution in which the magnetic field strength is 0 near the center in the conveying direction of the magnet 8 and the absolute value of the magnetic field strength increases toward both ends of the magnet 8, like in FIG. 7.

As illustrated in FIG. 26, the AMR element 10 is located in a strong magnetic field strength region whose magnetic field strength in the spacing direction is within a predetermined range. The object to be detected 5 passes through in the strong magnetic field strength region so as to intersect with the magnetic field in the spacing direction.

In FIG. 26, in a cross magnetic field that is orthogonal to the conveying direction and in which the AMR element 10 is disposed, the spacing direction magnetic field component from the north pole of the magnet 8 to the magnetic body 80 is the main magnetic field component of the magnetic field lines 17. The magnetic sensor device according to the Eighth Embodiment is also able to detect the object to be detected 5 such as paper money in the same principle as that used by the magnetic sensor device according to the First Embodiment in FIG. 8.

In the magnetic sensor device according to the Eighth Embodiment, like the magnetic sensor device according to the Fourth Embodiment, the bias magnet is disposed at only one side and a soft magnetic body such as iron is disposed at the other side, which reduces production cost of the magnetic sensor device.

If, like the magnetic sensor device according to the Fifth Embodiment, yokes for a magnet that are a pair of magnetic bodies, each being in contact with each of side surfaces that are orthogonal to the conveying direction, of side surfaces of the magnet 8, are disposed in the magnetic sensor device according to the Eighth Embodiment, the same effects as those of the magnetic sensor device according to the Fifth Embodiment are obtained.

If the magnetization direction of the magnet 8 of the magnetic sensor device according to the Eighth Embodiment is the spacing direction like the magnetic sensor device according to the Sixth Embodiment, the same effects as those of the magnetic sensor device according to the Sixth Embodiment are obtained.

Ninth Embodiment

Figure 27:
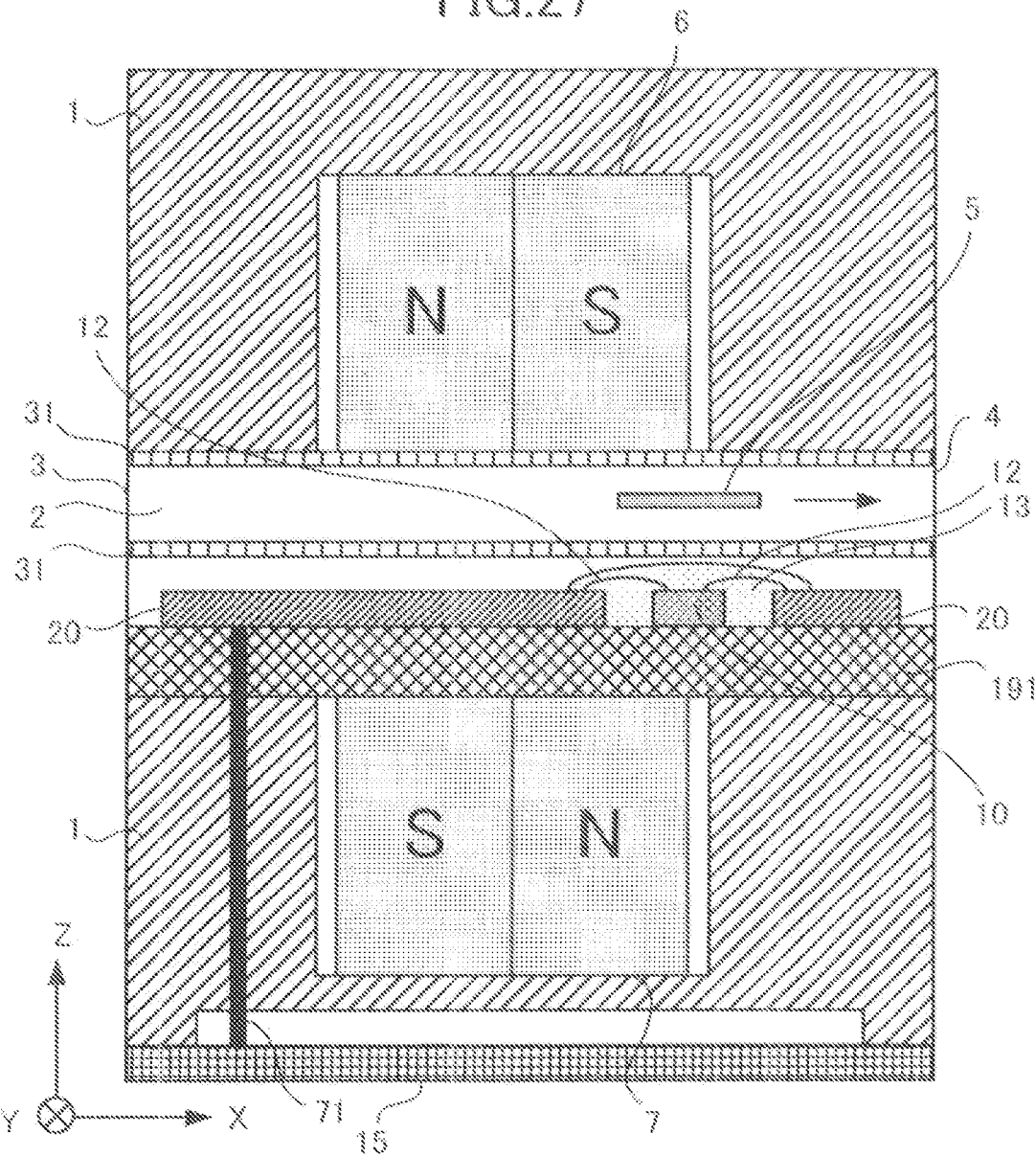
FIG. 27 is a cross-sectional view along the conveying direction of a magnetic sensor device according to Ninth Embodiment of the present invention.
Figure 28:
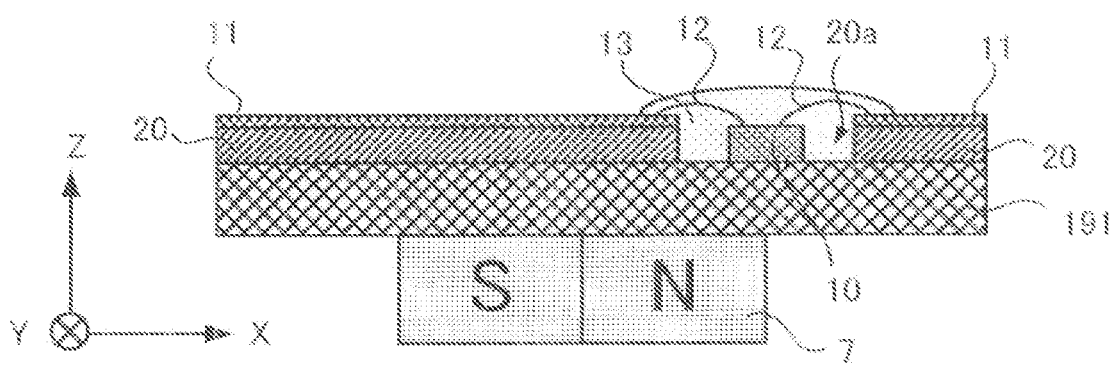
FIG. 28 is an enlarged view illustrating a state in which a monolayer board and an AMR element are mounted on a metal carrier in the magnetic sensor device according to the Ninth Embodiment.

FIG. 27 is a cross-sectional view along the conveying direction of a magnetic sensor device according to Ninth Embodiment of the present invention. FIG. 28 is an enlarged view illustrating a state in which a monolayer board and an AMR element are mounted on a metal carrier in the magnetic sensor device according to the Ninth Embodiment. In FIGS. 27 and 28, the same components as those in FIGS. 1 and 3 have the same reference signs. The magnetic sensor device according to the Ninth Embodiment includes a monolayer board 20, instead of the multilayer board 9 of the magnetic sensor device according to the First Embodiment.

On the surface of the metal carrier 191 are provided the monolayer board 20 and the AMR element 10. The monolayer board 20 includes a hole 20a. The AMR element 10 is bonded with adhesive to the surface of the metal carrier 191, exposed to the hole 20a, and is surrounded by the monolayer board 20. Like in FIG. 4, the electrodes 101a to 101c of the AMR element 10 are connected via the metal wires 12 to the electrodes 111a to 111c provided on the surface of the monolayer board 20, respectively. The electrodes 111a to 111c are connected via the transmission line 11 to the connection pads 112a to 112c provided on the back surface of the monolayer board 20. The connection pad 112a is connected to the DC power supply voltage Vcc, the connection pad 112b is connected to the processing circuit 15, and the connection pad 112c is DC grounded. The AMR element 10 and the metal wires 12 are sealed and protected by the resin 13.

In the magnetic sensor device according to the Ninth Embodiment, the same effects as those of the magnetic sensor device according to the First Embodiment are obtained.

Tenth Embodiment

Figure 29:
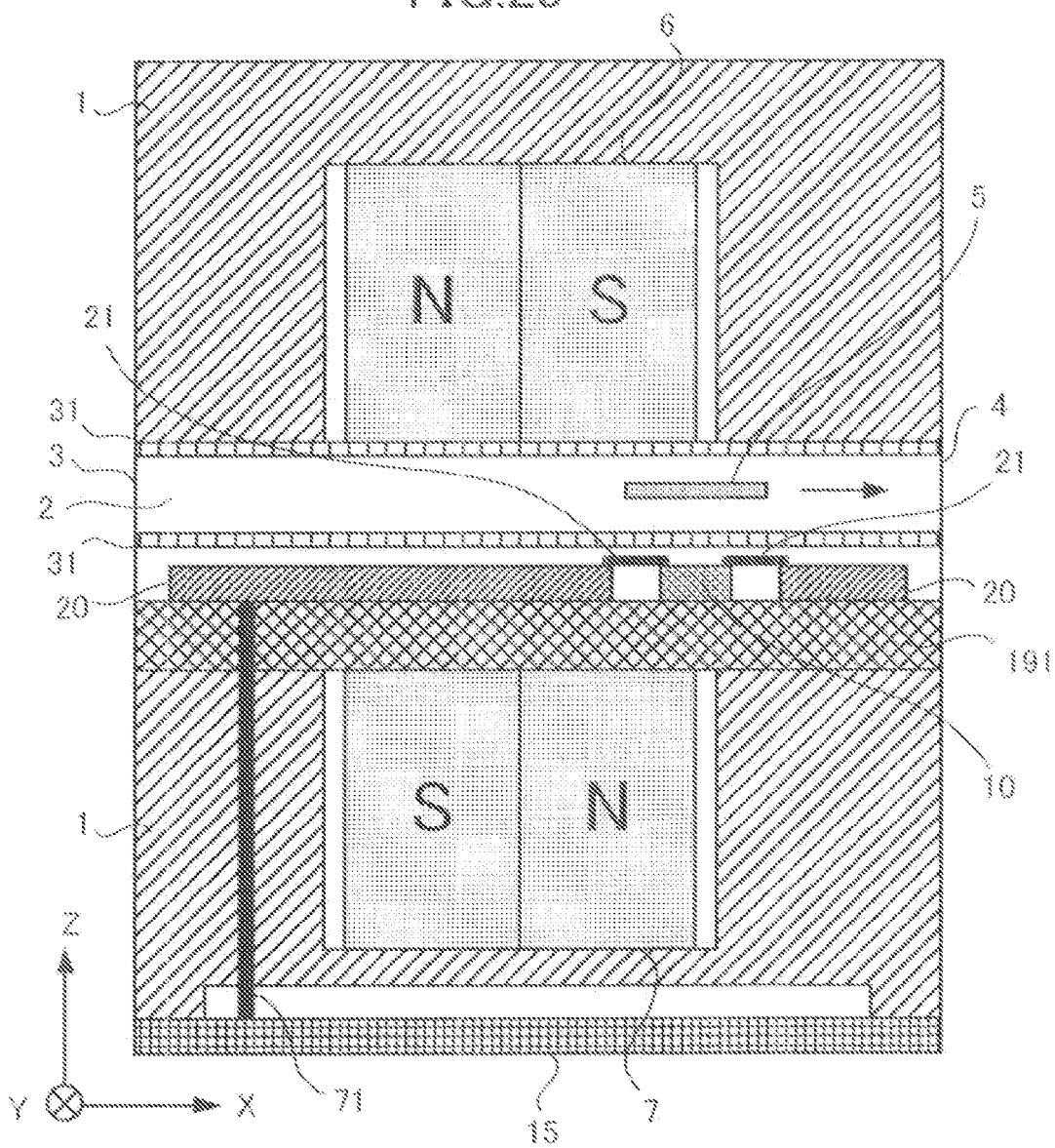
FIG. 29 is a cross-sectional view along the conveying direction of a magnetic sensor device according to Tenth Embodiment of the present invention.
Figure 30:
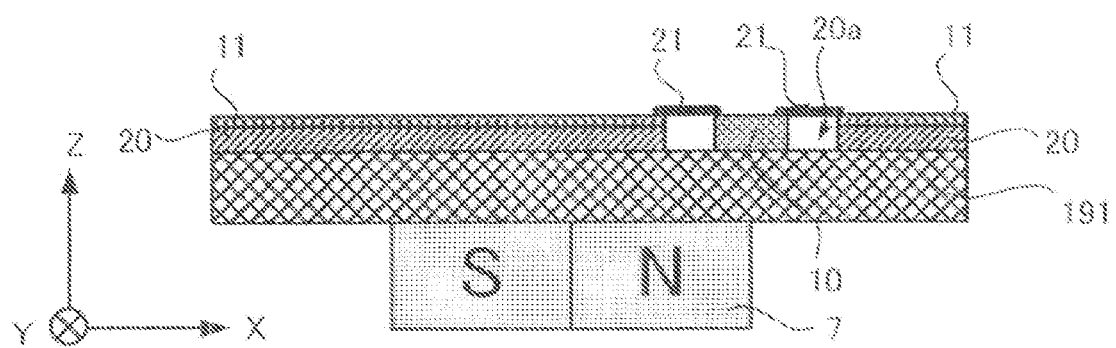
FIG. 30 is an enlarged view illustrating a state in which a monolayer board and an AMR element are mounted on a metal carrier in the magnetic sensor device according to the Tenth Embodiment.

FIG. 29 is a cross-sectional view along the conveying direction of a magnetic sensor device according to Tenth Embodiment of the present invention. FIG. 30 is an enlarged view illustrating a state in which a monolayer board and an AMR element are mounted on a metal carrier in the magnetic sensor device according to the Tenth Embodiment. In FIGS. 29 and 30, the same components as those in FIGS. 1 and 3 have the same reference signs. The magnetic sensor device according to the Tenth Embodiment includes the monolayer board 20, instead of the multilayer board 9 of the magnetic sensor device according to the First Embodiment.

On the surface of the metal carrier 191 are provided the monolayer board 20 and the AMR element 10. The monolayer board 20 includes the hole 20a. The AMR element 10 is bonded with adhesive to the surface of the metal carrier 191, exposed to the hole 20a, and is surrounded by the monolayer board 20. Like in FIG. 4, the electrodes 101a to 101c of the AMR element 10 are connected via metal tabs 21 to the electrodes 111a to 111c provided on the surface of the monolayer board 20, respectively. The electrodes 111a to 111c are connected via the transmission line 11 to the connection pads 112a to 112c provided on the back surface of the monolayer board 20. The connection pad 112a is connected to the DC power supply voltage Vcc, the connection pad 112b is connected to the processing circuit 15, and the connection pad 112c is DC grounded.

In the magnetic sensor device according to the Tenth Embodiment, the same effects as those of the magnetic sensor device according to the First Embodiment are obtained. Further, since the electrodes 101a to 101c of the AMR element 10 and the electrodes 111a to 111c provided on the surface of the monolayer board 20 are connected via the metal tabs 21, the space between the AMR element 10 and the electric shield 31 is smaller, reducing the distance between the AMR element 10 and the object to be detected 5, which increases output from the AMR element 10 and, thereby, improving the detection sensitivity.

Eleventh Embodiment

Figure 31:
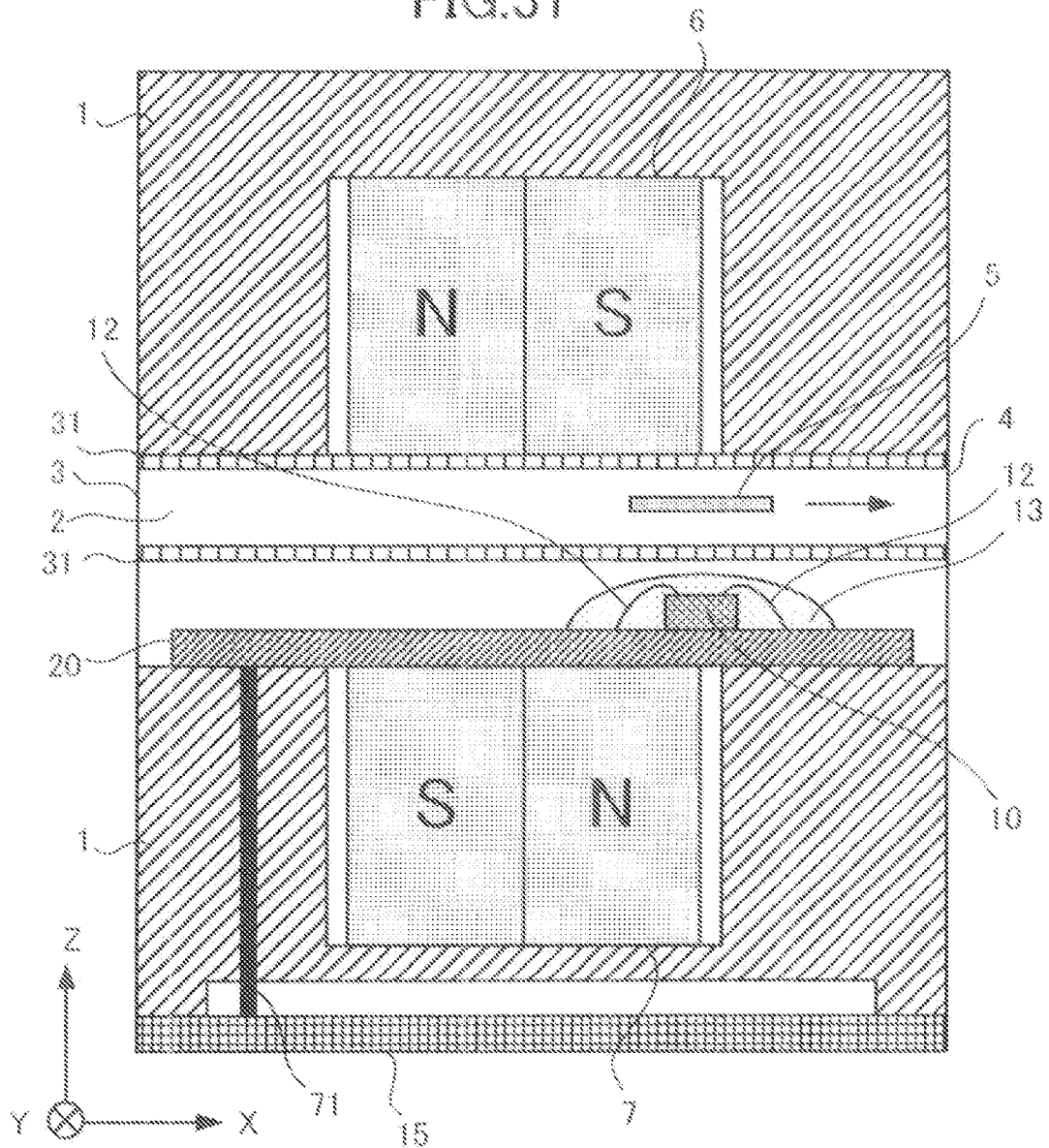
FIG. 31 is a cross-sectional view along the conveying direction of a magnetic sensor device according to Eleventh Embodiment of the present invention.
Figure 32:
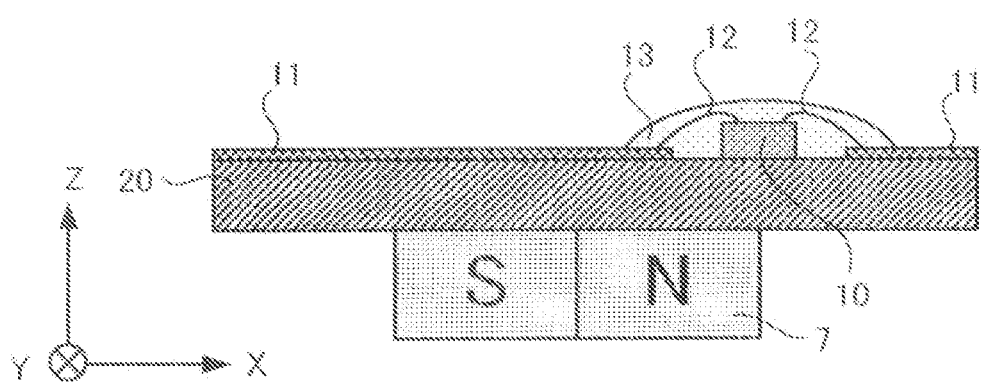
FIG. 32 is an enlarged view illustrating a state in which a monolayer board and an AMR element are mounted in the magnetic sensor device according to the Eleventh Embodiment.

FIG. 31 is a cross-sectional view along the conveying direction of a magnetic sensor device according to Eleventh Embodiment of the present invention. FIG. 32 is an enlarged view illustrating a state in which a monolayer board and an AMR element are mounted in the magnetic sensor device according to the Eleventh Embodiment. In FIGS. 31 and 32, the same components as those in FIGS. 1 and 3 have the same reference signs. The magnetic sensor device according to the Eleventh Embodiment includes the monolayer board 20, instead of the multilayer board 9 of the magnetic sensor device according to the First Embodiment. The magnetic sensor device according to the Eleventh Embodiment does not include the metal carrier 191.

The AMR element 10 is bonded with adhesive to the surface of the monolayer board 20. Like in FIG. 4, the electrodes 101a to 101c of the AMR element 10 are connected via the metal wires 12 to the electrodes 111a to 111c provided on the monolayer board 20, respectively. The electrodes 111a to 111c are connected via the transmission line 11 to the connection pads 112a to 112c provided on the back surface of the monolayer board 20. The connection pad 112a is connected to the DC power supply voltage Vcc, the connection pad 112b is connected to the processing circuit 15, and the connection pad 112c is DC grounded. The AMR element 10 and the metal wires 12 are sealed and protected by the resin 13.

In the magnetic sensor device according to the Eleventh Embodiment, the same effects as those of the magnetic sensor device according to the First Embodiment are obtained. Since the metal carrier 191 is not provided, the structure of the magnetic sensor device is simplified.

Twelfth Embodiment

Figure 33:
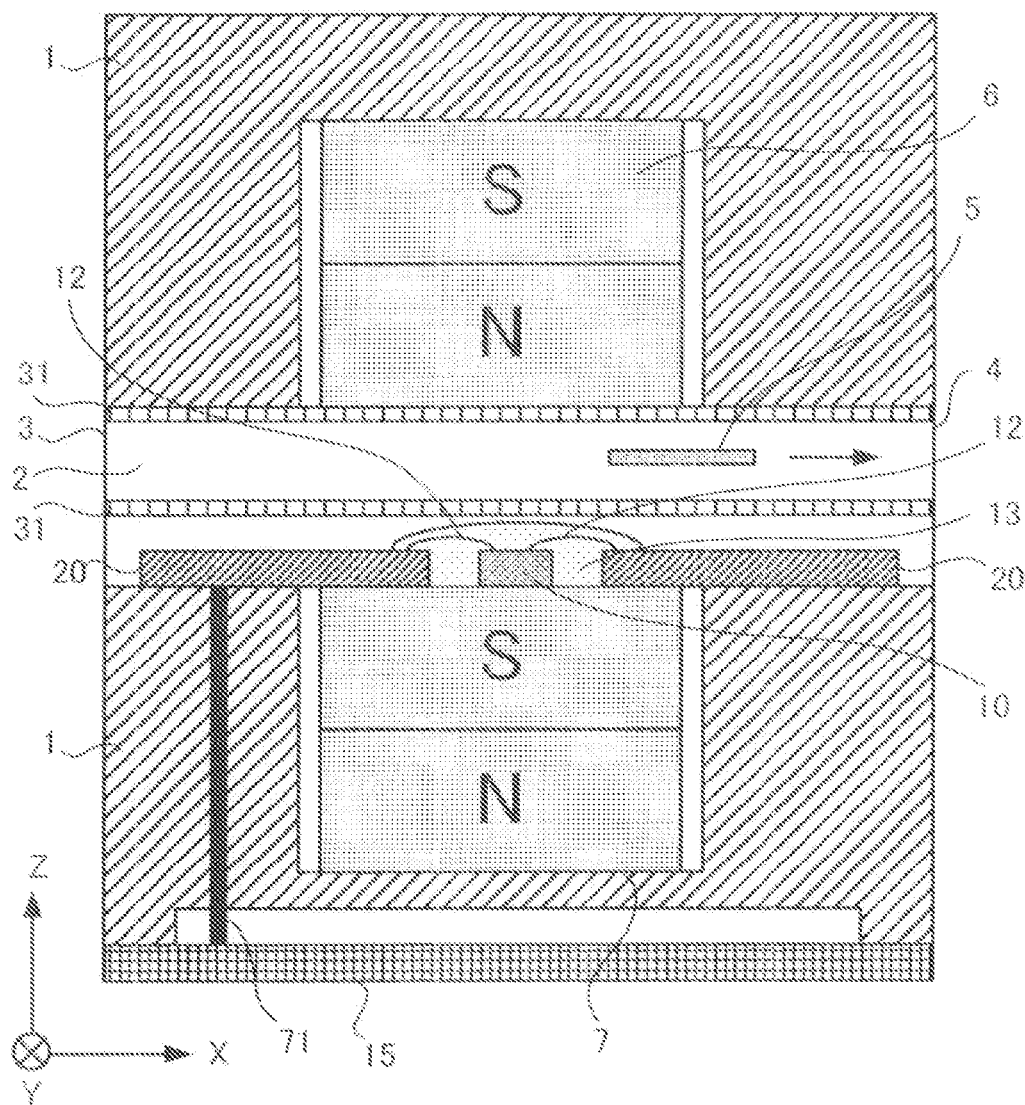
FIG. 33 is a cross-sectional view along the conveying direction of a magnetic sensor device according to Twelfth Embodiment of the present invention.
Figure 34:
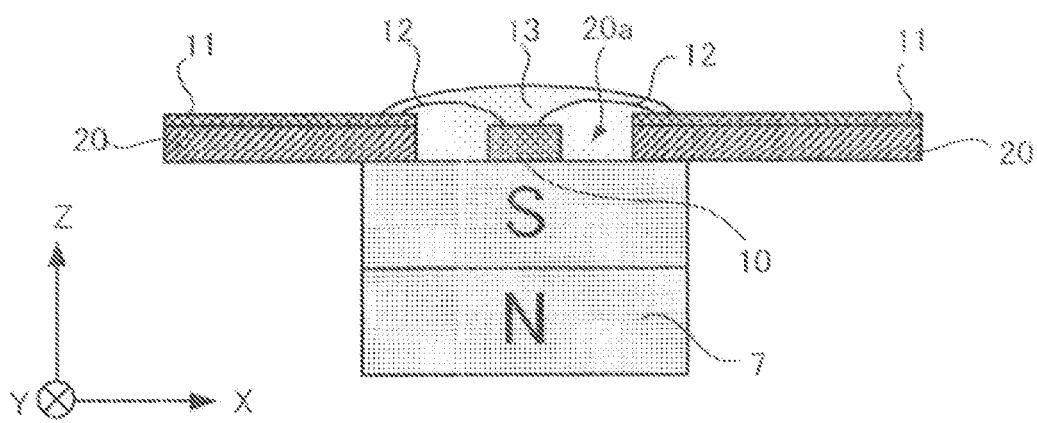
FIG. 34 is an enlarged view illustrating a state in which a monolayer board and an AMR element are mounted in the magnetic sensor device according to the Twelfth Embodiment.

FIG. 33 is a cross-sectional view along the conveying direction of a magnetic sensor device according to Twelfth Embodiment of the present invention. In the magnetic sensor device according to the Twelfth Embodiment, orientations of the first magnet 6 and the second magnet 7 of the magnetic sensor device according to the Eleventh Embodiment are changed so that either one of the poles of the first magnet 6 faces an opposite pole of the second magnet 7. Then, the AMR element 10 is provided on the surface of the second magnet 7, and is surrounded by the monolayer board 20. FIG. 34 is an enlarged view illustrating a state in which a monolayer board and an AMR element are mounted in the magnetic sensor device according to the Twelfth Embodiment. In FIGS. 33 and 34, the same components as those in FIGS. 31 and 32 have the same reference signs.

The monolayer board 20 is secured to the second magnet 7, and has the hole 20a. The AMR element 10 is bonded with adhesive to the surface of the second magnet 7, exposed to the hole 20a, and is surrounded by the monolayer board 20. Like in FIG. 4, the electrodes 101a to 101c of the AMR element 10 are connected via the metal wires 12 to the electrodes 111a to 111c provided on the surface of the monolayer board 20, respectively. The electrodes 111a to 111c are connected via the transmission line 11 to the connection pads 112a to 112c provided on the back surface of the monolayer board 20. The connection pad 112a is connected to the DC power supply voltage Vcc, the connection pad 112b is connected to the processing circuit 15, and the connection pad 112c is DC grounded. The AMR element 10 and the metal wires 12 are sealed and protected by the resin 13.

Since different poles of the first magnet 6 and the second magnet 7 face each other, a magnetic field in the conveying direction is applied on the object to be detected 5 and the AMR element 10, like in FIG. 23, thereby obtaining the same effects as those of the magnetic sensor device according to the Sixth Embodiment.

Thirteenth Embodiment

Figure 35:
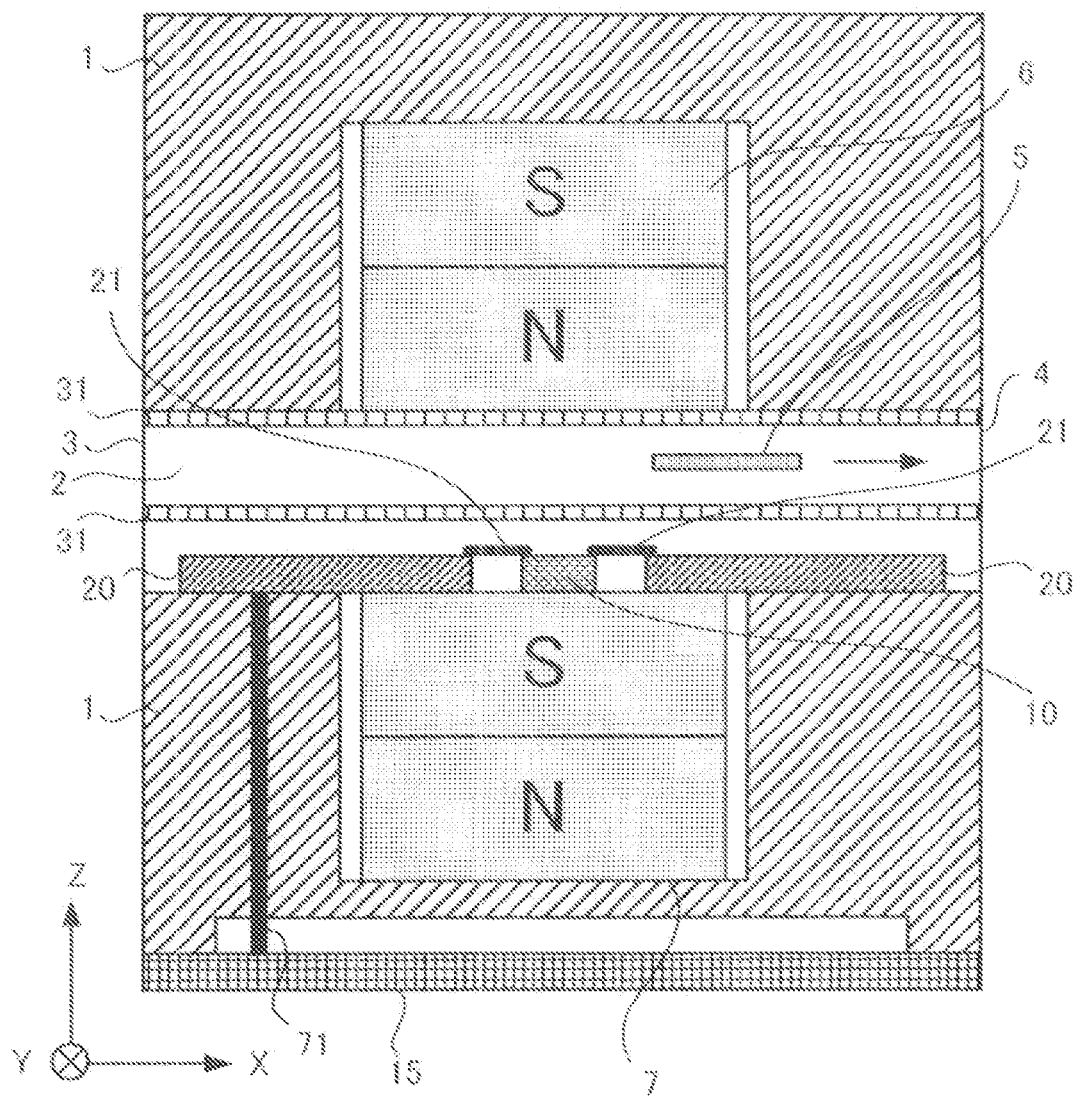
FIG. 35 is a cross-sectional view along the conveying direction of a magnetic sensor device according to Thirteenth Embodiment of the present invention.
Figure 36:
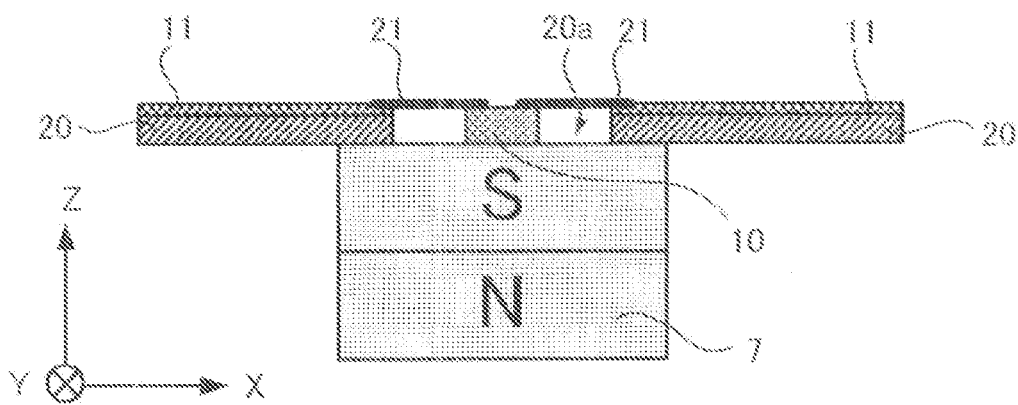
FIG. 36 is an enlarged view illustrating a state in which a monolayer board and an AMR element are mounted in the magnetic sensor device according to the Thirteenth Embodiment.

FIG. 35 is a cross-sectional view along the conveying direction of a magnetic sensor device according to Thirteenth Embodiment of the present invention. In FIG. 35, instead of the metal wires 12 of the magnetic sensor device according to the Twelfth Embodiment, the metal tabs 21 connect the electrodes 101a to 101c of the AMR element 10 to the electrodes 111a to 111c provided on the surface of the monolayer board 20. FIG. 36 is an enlarged view illustrating a state in which a monolayer board and an AMR element are mounted in the magnetic sensor device according to the Thirteenth Embodiment. In FIGS. 35 and 36, the same components as those in FIGS. 33 and 34 have the same reference signs.

The monolayer board 20 is secured to the second magnet 7, and has the hole 20a. The AMR element 10 is bonded with adhesive to the surface of the second magnet 7, exposed to the hole 20a, and is surrounded by the monolayer board 20. Like in FIG. 4, the electrodes 101a to 101c of the AMR element 10 are connected via the metal tabs 21 to the electrodes 111a to 111c provided on the surface of the monolayer board 20, respectively. The electrodes 111a to 111c are connected via the transmission line 11 to the connection pads 112a to 112c provided on the back surface of the monolayer board 20. The connection pad 112a is connected to the DC power supply voltage Vcc, the connection pad 112b is connected to the processing circuit 15, and the connection pad 112c is DC grounded.

Since different poles of the first magnet 6 and the second magnet 7 face each other, a magnetic field in the conveying direction is applied on the object to be detected 5 and the AMR element 10, like in FIG. 23, thereby obtaining the same effects as those of the magnetic sensor device according to the Sixth Embodiment. Further, the electrodes 101a to 101c of the AMR element 10 and the electrodes 111a to 111c provided on the surface of the monolayer board 20 are connected via the metal tabs 21. Therefore, space between the AMR element 10 and the electric shield 31 is smaller, reducing the distance between the AMR element 10 and the object to be detected 5, which increases output from the AMR element 10 and, thereby improving detection sensitivity.

The above embodiments can be modified within the principle of the present invention. The above embodiments are for describing the present invention, and are not intended to limit the scope of the present invention. The scope of the present invention is defined by claims, not by the above embodiments. Various modifications made within claims and equivalents to claims are included in the scope of the present invention.

This application claims priority based on Japanese Patent Application No. 2011-109628 filed on May 16, 2011, that includes the specification, claims, drawings and abstract, and Japanese Patent Application No. 2012-077356 filed on Mar. 29, 2012, that includes the specification, claims, drawings and abstract. The disclosure of both is incorporated herein by reference.

INDUSTRIAL APPLICABILITY

The present invention can be preferably applied to a magnetic sensor device that detects the magnetic pattern of an object to be detected in the case where the object to be detected having the magnetic pattern and a magnetoresistance effect element are not in contact with each other, that is, apart from each other by a predetermined distance.

REFERENCE SIGNS LIST

1. Housing
2. Conveyance path
3. First slit
4. Second slit
5. Object to be detected
6. First magnet
7. Second magnet
8. Magnet
9. Multilayer board
9a. Hole
10. AMR element
11. Transmission line
12. Metal wire
13. Resin
15. Processing circuit
17. Magnetic field line
20. Monolayer board
20a Hole
21 Metal tab
31 Electric shield
71 Cable
80 Magnetic body
81 Yoke for first magnet
82 Yoke for second magnet
83 Yoke for magnet
91 First layer board
91a Hole of first layer board
92 Second layer board
92a Hole of second layer board
101a, 101b, 101c Electrode
102a, 102b Resistor
111a, 111b, 111c Electrode
112a, 112b, 112c Contact pad
191 Metal carrier

The invention claimed is:

1. A magnetic sensor device comprising:
a conveyance path for conveying an object to be detected having a magnetic pattern;
a magnet having poles each facing the conveyance path;
first magnetic bodies each in contact with each of side surfaces orthogonal to the conveying direction of the object to be detected, of side surfaces of the magnet;
at least one second magnetic body located on a side opposite to the first magnetic bodies with respect to the conveyance path;
a magnetoresistance effect element located between the second magnetic body and the conveyance path in a cross magnetic field that has magnetic field strength within a predetermined range in a spacing direction and that is generated by the first magnetic bodies and the second magnetic body, the magnetoresistance effect element to detect, as change in the resistance value, change in a component in the conveying direction in the cross magnetic field, the change being caused by the magnetic pattern of the object to be detected, the spacing direction being a direction orthogonal to the conveying direction in the conveyance path and being a direction that vertically passes through the magnetic pattern; and
an outputter connected to the magnetoresistance effect element, the outputter to output the change in the resistance value detected by the magnetoresistance effect element.

2. The magnetic sensor device according to claim 1, further comprising:
a second magnet, wherein
the magnet is a first magnet,
the first magnet and the second magnet are located on mutually opposing sides of the conveyance path, and each pole of the first magnet faces each opposite pole of the second magnet;
the first magnetic bodies are paired yokes for the first magnet, each yoke being in contact with each of side surfaces orthogonal to the conveying direction, of side surfaces of the first magnet, and
the at least one second magnetic body are paired yokes for the second magnet, each yoke being in contact with each of side surfaces orthogonal to the conveying direction, of side surfaces of the second magnet.

3. The magnetic sensor device according to claim 1, wherein
the poles of the magnet each face the second magnetic body, and
the first magnetic bodies are paired yokes for the magnet, each yoke being in contact with each of side surfaces orthogonal to the conveying direction, of side surfaces of the magnet.

* * * * *